US012180463B2

(12) United States Patent
Walter

(10) Patent No.: US 12,180,463 B2
(45) Date of Patent: Dec. 31, 2024

(54) LACTOBACILLUS REUTERI

(71) Applicant: PRECISIONBIOTICS GROUP LIMITED, Cork (IE)

(72) Inventor: Jens Walter, Cork (IE)

(73) Assignee: PRECISIONBIOTICS GROUP LIMITED, Cork (IE)

( * ) Notice: Subject to any disclaimer, the term of this patent is extended or adjusted under 35 U.S.C. 154(b) by 421 days.

(21) Appl. No.: 17/763,542

(22) PCT Filed: Sep. 24, 2020

(86) PCT No.: PCT/EP2020/076792
§ 371 (c)(1),
(2) Date: Mar. 24, 2022

(87) PCT Pub. No.: WO2021/058688
PCT Pub. Date: Apr. 1, 2021

(65) Prior Publication Data
US 2023/0146454 A1    May 11, 2023

(30) Foreign Application Priority Data

Sep. 26, 2019 (EP) .................................... 19199823
Mar. 6, 2020 (EP) .................................... 20161520

(51) Int. Cl.
| | |
|---|---|
| *C12N 1/20* | (2006.01) |
| *A23L 33/00* | (2016.01) |
| *A23L 33/105* | (2016.01) |
| *A23L 33/125* | (2016.01) |
| *A23L 33/135* | (2016.01) |
| *A61K 35/747* | (2015.01) |
| *C12R 1/225* | (2006.01) |

(52) U.S. Cl.
CPC ............ *C12N 1/205* (2021.05); *A23L 33/105* (2016.08); *A23L 33/125* (2016.08); *A23L 33/135* (2016.08); *A23L 33/40* (2016.08); *A61K 35/747* (2013.01); *A23V 2400/173* (2023.08); *C12R 2001/225* (2021.05)

(58) Field of Classification Search
CPC ..... C12N 1/205; A23L 33/105; A23L 33/125; A23L 33/40; A61K 35/747; A23V 2400/173
See application file for complete search history.

(56) References Cited

U.S. PATENT DOCUMENTS

2008/0254011 A1   10/2008   Rothschild et al.
2014/0065696 A1   3/2014   Saulnier et al.

FOREIGN PATENT DOCUMENTS

KR   101951919 B1   2/2019

OTHER PUBLICATIONS

Valeur et al. 2004 (Colonization and Immunomodulation by Lactobacillus reuteri ATCC 55730 in the Human Gastrointestinal Tract; Applied and Environmental Microbiology 70(2): 1176-1181). (Year: 2004).*
Abrahamsson, T.R. et al., "Low Diversity Of The Gut Microbiota In Infants With Atopic Eczema", *Journal Allergy Clinical Immunology*, vol. 129, No. 2, pp. 434-440 (Feb. 2012).
Bene, K.P. et al., "Lactobacillus Reuteri Surface Mucus Adhesins Upregulate Inflammatory Responses Through Interactions With Innate C-Type Lectin Receptors", *Frontiers In Microbiology*, vol. 8, Article 321, pp. 1-16 (Mar. 2017).
Bisgaard, H. et al., Reduced Diversity Of The Intestinal Microbiota During Infancy Is Associated With Increased Risk Of Allergic Disease At School Age, *Journal Allergy Clinical Immunology*, vol. 128, No. 3, pp. 646-652 (Sep. 2011).
Blaser, M.J. et al., "What Are The Consequences Of The Disappearing Human Microbiota?", *Nature Reviews Microbiology*, vol. 7, pp. 887-894 (Dec. 2009).
Buffington, S.A. et al., "Microbial Reconstitution Reverses Maternal Diet-Induced Social And Synaptic Deficits In Offspring", *Cell 165*, pp. 1762-1775 (Jun. 2016).
Carver, T. et al., "Artemis: An Integrated Platform For Visualization And Analysis Of High-Throughput Sequence-Based Experimental Data", *Artemis*, vol. 28, No. 4, pp. 464-469 (Dec. 2011).
Duar, R.M., "Experimental Evaluation Of Host Adaption Of Lactobacillus Reuteri To Different Vertebrate Species", *Applied And Environmental Microbiology*, vol. 83, Issue 12, pp. 1-17 (Jun. 2017).
Frese, S.A., "The Evolution Of Host Specialization In The Vertebrate Gut Symbiont Lactobacillus Reuteri", *PLoS Genetics*, vol. 7, Issue 2, pp. 1-16 (Feb. 2011).
Frese, S.A., "Molecular Characterization Of Host-Specific Biofilm Formation In A Vertebrate Gut Symbiont", *PLoS Genetics*, vol. 9, Issue 12, pp. 1-13 (Dec. 2013).
Haahtela, T., "Hunt For The Origin Of Allergy—Comparing The Finnish And Russian Karelia", *Clinical & Experimental Allergy*, vol. 45, Issue 5 (May 2015).
Hanski, I., "Environmental Biodiversity, Human Microbiota, And Allergy Are Interrelated", *PNAS*, vol. 109, No. 21 pp. 8334-8339 (May 2012).
He, B., "Resetting Microbiota By *Lactobacillus reuteri* Inhibits T Reg Deficiency-Induced Autoimmunity Via Adenosine $A_{2A}$ Receptors", *Journal Exp. Med.*, vol. 214, No. 1 pp. 107-123 (2017).
Jarchum, I., "Regulation Of Innate And Adaptive Immunity By The Commensal Microbiota", *Elsevier, Current Opinion In Immunology*, vol. 23, pp. 353-360 (2011).
Kell, D.B., Viability And Activity In Readily Culturable Bacteria: A Review And Discussion Of The Practical Issues, *Kluwer Academic Publishers*, vol. 73, pp. 169-187 (1998).

(Continued)

*Primary Examiner* — Mary Maille Lyons
(74) *Attorney, Agent, or Firm* — Bookoff McAndrews, PLLC

(57) ABSTRACT

*Lactobacillus reuteri* strain having NCIMB accession number 42835 is from a novel phylogenetic clade and has unique immune-stimulatory properties and enhanced ecological performance in the human gut. A substrate for the strain, such as raffinose, may be administered at the same time as or separately from the strain.

19 Claims, 10 Drawing Sheets

Specification includes a Sequence Listing.

(56) References Cited

OTHER PUBLICATIONS

Lamas, B. et al., "CARD9 Impacts Colitis By Altering Gut Microbiota Metabolism Of Tryptophan Into Aryl Hydrocarbon Receptor Ligands", *Nature Medicine*, vol. 22, No. 6, pp. 598-609 (Jun. 2016).
Lisciandro, J.G. et al., "Comparison Of Neonatal T Regulatory Cell Function In Papua New Guinean And Australian Newborns", *Pediatric Allergy Immunology* (2011).
Lisciandro, J.G. et al., "Neonatal Antigen-Presenting Cells Are Functionally More Quiescent In Children Born Under Traditional Compared With Modern Environmental Conditions", *Journal of Allergy Clinical Immunology*, vol. 130, No. 5, pp. 1167-1174.e10 (Nov. 2012).
Liu, Y. et al., "*Lactobacillus reuteri* DSM 17938 Changes The Frequency Of Foxp3$^+$ Regulator T Cells In The Intestine And Mesenteric Lymph Node In Experimental Necrotizing Enterocolitis", *PLOS One*, vol. 8, Issue 2, pp. 1-10 (Feb. 2013).
Liu, Y. et al., "Therapeutic Effect Of *Lactobacillus reuteri* DSM 17938 On Treg-Deficiency-Induced Autoimmunity (IPEX Syndrome) Via The Inosine-Adenosine 2A Receptors", *The American Association of Immunologists, Inc.*, vol. 198, (May 2017).
Marsland, B., "Regulating Inflammation With Microbial Metabolites", *Nature Medicine*, vol. 22, No. 6, pp. 581-583 (Jun. 2016).
Martínez et al., "The Gut Microbiota Of Rural Papua New Guineans: Composition, Diversity Patterns, and Ecological Processes", vol. 11, pp. 527-538 (Apr. 2015).
Milani, C. et al., "Phylotype-Level Profiling Of Lactobacilli In Highly Complex Environments By Means Of An Internal Transcribed Spacer-Based Metagenomic Approach", *Applied And Environmental Microbiology*, vol. 84, Issue 14, pp. 1-14 (Jul. 2018).
Mitsuoka, T., "Intestinal Floral And Aging", *Nutrition Reviews*, vol. 50, No. 12, pp. 438-446, (Dec. 1992).
Jay, J.M. et al., "Modern Food Microbiology", *Springer*, 7$^{th}$ Edition, pp. 1-789 (2005).
Oh, P.L., Diversification Of The Gut Symbiont *Lactobacillus reuteri* As A Result Of Host-Driven Evolution, *The ISME Journal*, vol. 4, pp. 377-387 (2010).
Rattanaprasert, M., "Quantitative Evaluation Of Synbiotic Strategies To Improve Persistence And Metabolic Activity Of *Lactobacillus reuteri* DSM 17938 In The Human Gastrointestinal Tract", *Journal Of Functional Foods 10*, pp. 85-94 (2014).
Reuter, G., The Lactobacillus And Bifidobacterium Microflora Of The Human Intestine: Composition And Sucession, *Current Issues Intest. Microbiology*, vol. 2(2), pp. 43-53 (2001).
Rook, G., "2$^{nd}$ Gut Microbiota And Health Summit", May 2013, www.gutmicrobiotaforhealth.com/the-immune-system-is-like-an-army-an-interview-with-prof-graham-rook/.
Ruiz-Núñez, B. et al., "Lifestyle And Nutritional Imbalances Associated With Western Diseases: Causes And Consequences Of Chronic Systemic Low-Grade Inflammation In An Evolutionary Context", *Journal Of Nutritional Biochemistry*, vol. 24, pp. 1183-1201 (2013).
Segata, N., "Gut Microbiome: Westernization And The Disappearance Of Intestinal Diversity", *Current Biology* 25, pp. R600-R620 (Jul. 20, 2015).
Sinkiewicz, G. et al., "Influence Of Dietary Supplementation With Lactobacillus Reuteri On The Oral Flora Of Healthy Subjects", *Swed Dent J.*, vol. 34(4), pp. 197-206 (2010).
Sonnenburg, E.D. et al., "Starving Our Microbial Self: The Deleterious Consequences Of A Diet Deficient In Microbiota-Accessible Carbohydrates", *Cell Metabolism 20*, pp. 779-786 (Nov. 4, 2014).
Spinler, J.K. et al., From Prediction To Function Using Evolutionary Genomics: Human-Specific Ecotypes Of *Lactobacillus reuteri* Have Diverse Probiotic Functions, *Genome Biology Evolution*, vol. 6(7), pp. 1772-1789 (Jun. 19, 2014).
Tannock, G. W. et al., "Identification of Lactobacillus Isolates From The Gastrointestinal Tract, Silage, And Yoghurt by 16S-23S rRNA Gene Intergenic Spacer Region Sequence Comparisons", *Applied And Environmental Microbiology*, vol. 65, No. 9, pp. 4264-4267 (Sep. 1999).
Teixeira, J.S. et al., Levansucrase And Sucrose Phoshorylase Contribute To Raffinose, Stachyose, And Verbascose Metabolism By Lactobacilli, *Food Microbiology*, vol. 31, pp. 278-284 (2012).
Teixeira, J.S. et al., Functional Characterization Of Sucrose Phosphorylase And scrR, A Regulator Of Sucrose Metabolism In *Lactobacillus reuteri*, *Food Microbiology*, vol. 36, pp. 432-439 (2013).
Valeur, N. et al., "Colonization And Immunomodulation By Lactobacillus Reuteri ATCC 55730 In The Human Gastrointestinal Tract", *Applied And Environmental Microbiology*, vol. 70, No. 2, pp. 1176-1181 (Feb. 2004).
Van Nimwegen, F.A. et al., "Mode And Place Of Delivery, Gastrointestinal Microbiota, And Their Influence On Asthma And Atopy", *Journal Allergy Clinical Immunology*, vol. 128, No. 5, pp. 948-955. e3 (Nov. 2011).
Walter, Jens, "Ecological Role Of Lactobacilli In The Gastrointestinal Tract: Implications For Fundamental And Biomedical Research", *Applied And Environmental Microbiology*, vol. 74, No. 16, pp. 4985-4996 (Aug. 2008).
Walter, J. et al., Host-Microbial Symbiosis In The Vertebrate Gastrointestinal Tract And The *Lactobacillus reuteri* Paradigm, PNAS, vol. 108, Suppl. 1, pp. 4645-4652 (Mar. 15, 2011).
Wickens, K. et al., A Differential Effect Of 2 Probiotics In The Prevention Of Eczema And Atopy: A Double-Blind, Randomized, Placebo-Controlled Trial, *Journal Allergy Clinical Immunology*, vol. 122(4), pp. 788-794 (Oct. 2008).
Zelante, T. et al., Tryptophan Catabolites From Microbiota Engage Aryl Hydrocarbon Receptor And Balance Mucosal Reactivity Via Interleukin-22, *Immunity* 39, pp. 372-385 (Aug. 22, 2013).
Zhao, X. et al., Genetic And Phenotypic Analysis Of Carbohydrate Metabolism And Transport In *Lactobacillus reuteri*, *International Journal of Food Microbiology*, vol. 272, pp. 12-21 (2018).
International Search Report in PCT/EP2020/076792 dated, Dec. 1, 2020 (3 pages).

\* cited by examiner

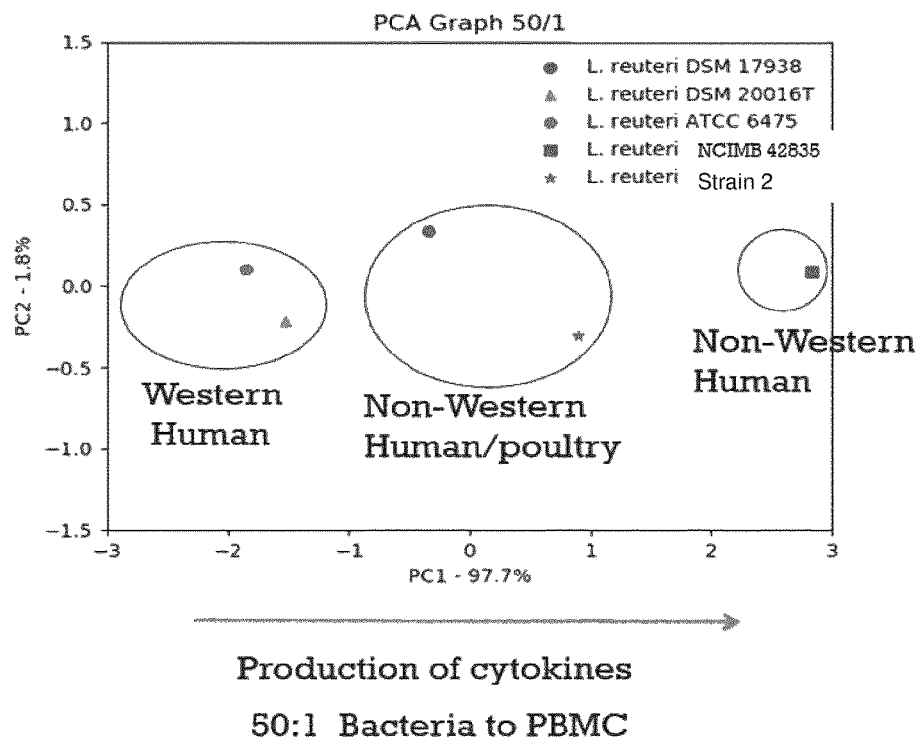
Fig. 8
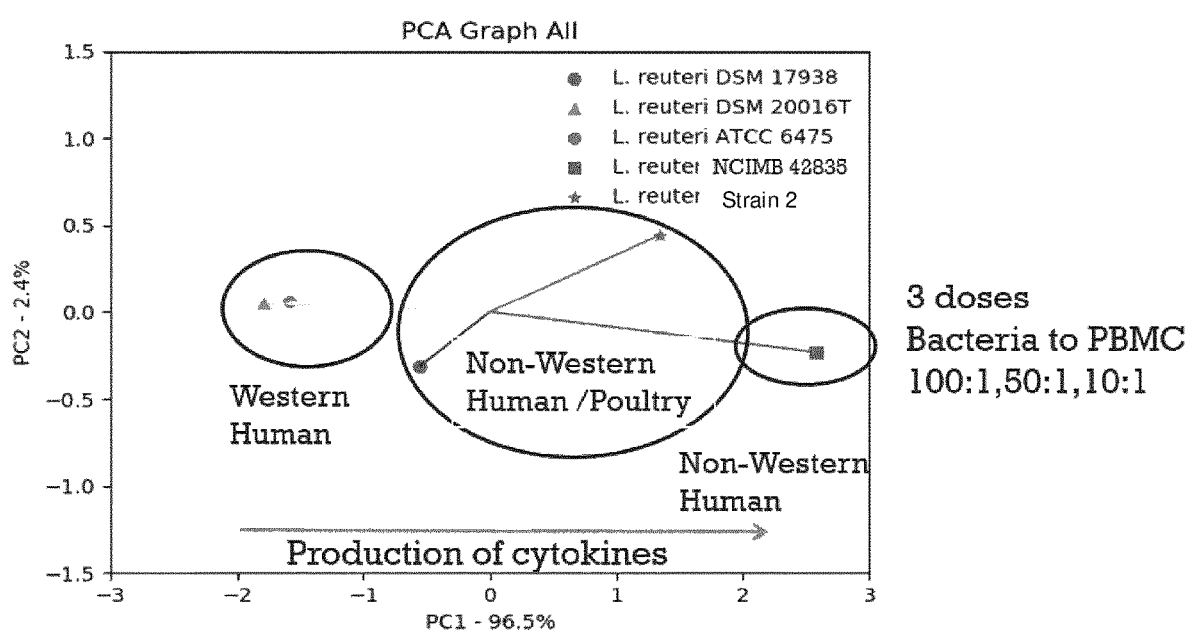

SEQUENCE LISTING

<160> NUMBER OF SEQ ID NOS: 9

<210> SEQ ID NO 1
<211> LENGTH: 18
<212> TYPE: DNA
<213> ORGANISM: Lactobacillus reuteri

<400> SEQUENCE: 1

-continued

```
agtttgatcc tggctcag                                                 18

<210> SEQ ID NO 2
<211> LENGTH: 15
<212> TYPE: DNA
<213> ORGANISM: Lactobacillus reuteri

<400> SEQUENCE: 2
taccttgtta cgact                                                    15

<210> SEQ ID NO 3
<211> LENGTH: 1575
<212> TYPE: DNA
<213> ORGANISM: Lactobacillus reuteri

<400> SEQUENCE: 3
ttatatattt tatatgagag tttgatcctg gctcaggatg aacgccggcg gtgtgcctaa   60
tacatgcaag tcgtacgcac tggcccaact gattgatggt gcttgcacct gattgacgat  120
ggatcaccag tgagtggcgg acgggtgagt aacacgtagg taacctgccc cggagcgggg  180
gataacattt ggaaacagat gctaataccg cataacaaca aaagccacat ggcttttgtt  240
tgaaagatgg ctttggctat cactctggga tggacctgcg gtgcattagc tagttggtaa  300
ggtaacggct taccaaggcg atgatgcata gccgagttga gagactgatc ggccacaatg  360
gaactgagac acggtccata ctcctacggg aggcagcagt agggaatctt ccacaatggg  420
cgcaagcctg atggagcaac accgcgtgag tgaagaaggg tttcggctcg taaagctctg  480
ttgttggaga agaacgtgcg tgagagtaac tgttcacgca gtgacggtat ccaaccagaa  540
agtcacggct aactacgtgc cagcagccgc ggtaatacgt aggtggcaag cgttatccgg  600
atttattggg cgtaaagcga gcgcaggcgg ttgcttaggt ctgatgtgaa agccttcggc  660
ttaaccgaag aagtgcatcg gaaaccgggc gacttgagtg cagaagagga cagtggaact  720
ccatgtgtag cggtggaatg cgtagatata tggaagaaca ccagtggcga aggcggctgt  780
ctggtctgca actgacgctg aggctcgaaa gcatgggtag cgaacaggat tagataccct  840
ggtagtccat gccgtaaacg atgagtgcta ggtgttggag ggtttccgcc cttcagtgcc  900
ggagctaacg cattaagcac tccgcctggg gagtacgacc gcaaggttga aactcaaagg  960
aattgacggg ggcccgcaca gcggtggagc atgtggttt aattcgaagc tacgcgaaga 1020
accttaccag gtcttgacat cttgcgctaa ccttagagat aaggcgttcc cttcggggac 1080
gcaatgacag gtggtgcatg gtcgtcgtca gctcgtgtcg tgagatgttg ggttaagtcc 1140
cgcaacgagc gcaacccttg ttactagttg ccagcattaa gttgggcact ctagtgagac 1200
tgccggtgac aaaccggagg aaggtgggga cgacgtcaga tcatcatgcc ccttatgacc 1260
tgggctacac acgtgctaca atggacggta caacgagtcg caaactcgcg agagcaagct 1320
aatctcttaa agccgttctc agttcggact gtaggctgca actcgcctac acgaagtcgg 1380
aatcgctagt aatcgcggat cagcatgccg cggtgaatac gttcccgggc cttgtacaca 1440
ccgcccgtca caccatggga gtttgtaacg cccaaagtcg gtggcctaac ctttatggag 1500
ggagccgcct aaggcgggac agatgactgg ggtgaagtcg taacaaggta gccgtaggaa 1560
acctgcggct ggatc                                                  1575

<210> SEQ ID NO 4
<211> LENGTH: 20
<212> TYPE: DNA
```

<210> SEQ ID NO 4
<211> LENGTH: 20
<212> TYPE: DNA
<213> ORGANISM: Lactobacillus reuteri

<400> SEQUENCE: 4
cgtaacaagg tagccgtagg    20

<210> SEQ ID NO 5
<211> LENGTH: 18
<212> TYPE: DNA
<213> ORGANISM: Lactobacillus reuteri

<400> SEQUENCE: 5
gtyvcgtcct tcwtcgsc    18

<210> SEQ ID NO 6
<211> LENGTH: 273
<212> TYPE: DNA
<213> ORGANISM: Lactobacillus reuteri

<400> SEQUENCE: 6
tagtaccaag gcattcacca tgcgcccttc ataacttaac ctaaacaatc aaagattgtc    60
tgattaattg agttagcgat tataattcgt taattaaaac tcaaataacg cggtgttctc    120
ggtttattgt tttgttaata agaaattag atagtattta gttttcaaag tacaagctct    180
gagggtaaac ccctcaaaac taaacaaagt ttctttgatg tgtaggttcc gttttattcc    240
ttagaaagga ggtgatccag ccgcaggttc tcc    273

<210> SEQ ID NO 7
<211> LENGTH: 16
<212> TYPE: DNA
<213> ORGANISM: Lactobacillus reuteri

<400> SEQUENCE: 7
gaatcgctag taatcg    16

<210> SEQ ID NO 8
<211> LENGTH: 17
<212> TYPE: DNA
<213> ORGANISM: Lactobacillus reuteri

<400> SEQUENCE: 8
gggttccccc attcgga    17

<210> SEQ ID NO 9
<211> LENGTH: 507
<212> TYPE: DNA
<213> ORGANISM: Lactobacillus reuteri

<400> SEQUENCE: 9
aatctccgga tcaaagcgta cttaccgctc cccgaagcat atcggtgtta gtcccgtcct    60
tcatcggctc ctagtaccaa ggcattcacc atgcgcccct cataacttaa cctaaacaat    120
caaagattgt ctgattaatt gagttagcga ttataattcg ttaattaaaa ctcaaataac    180
gcggtgttct cggtttattg ttttgttaat aaagaaatta gatagtattt agttttcaaa    240
gtacaagctc tgagggtaaa ccctcaaaa ctaaacaaag tttctttgat gtgtaggttc    300
cgttttattc cttagaaagg aggtgatcca gccgcaggtt ctcctacggc taccttgtta    360

```
cgacttcacc ccagtcatct gtcccgcctt aggcggctcc ctccataaag gttaggccac        420
cgactttggg cgttacaaac tcccatggtg tgacgggcgg tgtgtacaag gcccgggaac        480
gtattcaccg cggcatgctg atccgcg                                            507
```

LACTOBACILLUS REUTERI

CROSS-REFERENCE TO RELATED APPLICATIONS

This application is the U.S. national phase entry under 35 U.S.C. § 371 of International Application No. PCT/EP2020/076792, filed on Sep. 24, 2020, which claims the benefit of priority to European Application No. 19199823.6, filed Sep. 26, 2019, and to European Application No. 20161520.0, filed on Mar. 6, 2020.

This application contains a sequence listing, submitted electronically in ASCII format under the file name 00175-0016-00000_SL.txt, which is incorporated by reference herein in its entirety. The ASCII copy of the sequence listing was created on Jan. 11, 2023, and is 4,761 4,526 bytes in size.

FIELD OF THE INVENTION

The invention relates to *Lactobacillus reuteri* from a novel phylogenetic clade with unique immune-stimulatory properties and enhanced ecological performance in the human gut.

BACKGROUND OF THE INVENTION

The gut microbiota is a critical determinant of human health by directly contributing to pathologies, influencing host predisposition to disease. There is now substantial evidence that modern lifestyle and industrialization has resulted in a decrease in the bacterial diversity of the gut microbiota, likely due to a combination of factors such as use of antibiotics, modern clinical practices, sanitation, and change in dietary habits (Blaser & Falkow 2009; Segata, 2015). Increasing incidences of NCDs (non-communicable disease) in all parts of the world are linked to affluent lifestyles and are thought to result, at least in part, from loss of microbial diversity (Haahtela et al., 2015; Hanski et al., 2012; Rook, 2013). The mechanisms for these connections are unknown, and most focus has been on pathogenic microbes in concepts such as the 'hygiene hypothesis' (Jarchum et al., 2011). An alternative, and perhaps more plausible, hypothesis has been proposed that states that during human evolution, microbes have evolved into an essential role in regulating our immune system. The microbes involved are not infections, but friendly, symbiotic microbes which make up our human microbiome. These are acquired by exposure to other humans or animals and microbiota from our natural environment. Researchers now agree that a range of lifestyle changes including an increase in Caesarean section (C-section) births, less breast-feeding, smaller family sizes, and less time outdoors are underlying causes of reduced exposure to friendly microbes, whilst altered diet and antibiotics have adverse effects on the composition of the microbiome.

There is therefore a need to improve the bacterial diversity of the gut microbiota.

*L. reuteri* has been shown to be one of the truly indigenous bacteria of the human GI tract (Sinkiewicz, 2010). It naturally colonizes a wide range of vertebrates, including humans, pigs, hamsters, mice, rats, dogs, sheep, cattle, and different species of birds (including chickens), and it has also been found in the human urogenital tract and breast milk. (Mitsuoka, 1992).

The prevalence of *L. reuteri* is now very low in western human populations, where the species is only occasionally found (Walter J, 2008) There is some evidence that the prevalence of *L. reuteri* in human fecal samples was higher in the middle of the past century. Gerhard Reuter and Tomonari Mitsuoka, who in the 1960s and 1970s intensively studied the *Lactobacillus* biota of the human digestive tract, reported that *L. reuteri* was then one of the dominant lactobacilli and regularly detected (Mitsuoka T., 1992; Reuter G., 2001). The low prevalence in humans in more recent studies suggests a reduction of the *L. reuteri* population size during the past 50 years.

The term a "clade" (from Ancient Greek: κλάδος, klados, "branch"), also known as monophyletic group, is defined as a group of organisms that consists of a common ancestor and all its lineal descendants, and represents a single "branch" on the "tree of life".

The common ancestor may be an individual, a population, a species (extinct or extant), and so on right up to a kingdom and further. Clades are nested, one in another, as each branch in turn splits into smaller branches. These splits reflect evolutionary history as populations diverged and evolved independently.

The species *L. reuteri* represents the *L. reuteri* group in the heterofermentative clade of lactobacilli (Duar et. Al. 2017b). *L. reuteri* was thought to be well characterized genetically and physiologically, and metabolic traits that contribute to its ecological fitness in cereal and intestinal ecosystems are well understood (Zhao and Ganzle, 2018).

Human-derived *L. reuteri* strains belong to two distinct MLSA clades, designated clade II and VI. Clade II contains most human intestinal isolates and clusters together with isolates from ruminants, while human strains in clade VI are closely related to isolates from chickens (Oh, et al. 2010).

SUMMARY OF THE INVENTION

The invention provides a *Lactobacillus reuteri* strain with the NCIMB accession number 42835. An analysis of the genome of NCIMB 42835 versus other *L. reuteri* using 639 concatenated core genes of the species produces an Average Nucleotide Identity measurement (ANI) using the BLAST algorithm has shown that NCIMB 42835 has <97.5% similarity to the closest known strains of *L. reuteri*. Therefore, the strain differs significantly from currently known strains of the species *L. reuteri*.

Strain 42835 is a *Lactobacillus reuteri* from a novel phylogenetic clade with unique immune-stimulatory properties and enhanced ecological performance in the human gut.

A person skilled in the art would appreciate that strains can be identified by DNA sequence homology analysis with strain NCIMB 42835. Strains having a close sequence identity with strain NCIMB 42835 without demonstrable phenotypic or measurable functional differences are within the scope of the invention. A strain with a sequence identity (homology) of 97% or more, 97.5% or more, 97.75% or more, 98% or more, 98.25% or more, 98.5% or more, 98.75% or more, 99% or more, 99.25% or more, 99.5% or more, 99.75% or more with the DNA sequence of NCIMB 42835 are within the scope of the invention. Sequence homology may be determined using on-line homology algorithm "BLAST" program, publicly available at http://www.ncbi.nlm.nih.gov/BLAST/.

In one embodiment the strain is a human symbiont.

The invention provides *Lactobacillus reuteri* strain having NCIMB accession number 42835 or mutants or variants thereof.

The mutant may be a genetically modified strain of wild-type NCIMB 42835.

The variant may be a naturally occurring variant.

The strain may be in the form of a biologically pure culture.

Also provided is an isolated strain of *Lactobacillus reuteri* (NCIMB 42835).

The strain may be a probiotic.

In one case the strain is in the form of viable cells.

In another case the strain is in the form of non-viable cells.

The *Lactobacillus reuteri* strain NCIMB 42835 may be present in the formulation in an amount of more than $10^6$ cfu, typically from $10^7$ to $10^{10}$, typically from $10^8$ to $10^9$ cfu per dose. In one case the *Lactobacillus reuteri* strain NCIMB 42835 is present in the formulation in an amount of about $1 \times 10^9$ cfu per dose.

Bacterial viability reflects the number of culturable bacteria within a sample, i.e. the number of bacteria which retain the ability to reproduce when grown under optimal conditions (Viable cells).

Put another way, viability reflects the number of individual bacterial cells which retain the ability to replicate into larger bacterial colonies (colony forming units (CFUs)).

Viability is commonly determined using plate-counting methods, whereby a bacterial sample is diluted and then incubated on an agar plate containing the necessary nutrients for growth. Viability is then calculated from the number of bacterial colonies identified on a plate. Such methods are summarized in Modern Food Biology 2005 $7^{th}$ edition, James Monroe Jay, Martin J. Loessner, David A. Golden, Springer Science, New York.

Whilst plate-counting gives a good indication of viability, it does not encompass all living bacterial cells in the sample. (Kell, Douglas B., et al. "Viability and activity in readily culturable bacteria: a review and discussion of the practical issues." *Antonie van Leeuwenhoek* 73.2 (1998): 169-187).

Samples will also contain "viable but non-culturable" (VBNC) cells which remain metabolically active but have lost the ability to replicate at the time of analysis by plate count, and thus despite being alive will not form CFUs. Finally, samples will also contain dead cells. These two groups can be grouped together as "Non-Viable cells". Therefore, Non-viable cells are the inverse of Viable cells i.e. all those cells which have lost the ability to replicate when tested.

All samples containing Viable cells will also contain Non-Viable cells, therefore the definition of a Viable cell culture is clarified using CFU measurements.

All Non-Viable samples will contain at least VNBCs and possibly small amounts of Viable cells. Industry standard lower level detection limits of $10^3$ CFU/g viable cells allow for the inherent process variability caused by the presence of a certain number of VBNCs/Viable cells in Non-Viable samples.

In some embodiments, such as, but not limited to, special sterile food products or medicaments a non-replicating form of a probiotic strain may be preferable. For example, at least 95%, preferably at least 97%, more preferably at least 99% of the *Lactobacillus reuteri* strain can be non-replicating in the composition.

In one case the strain is significantly immunomodulatory following oral consumption in humans.

In one embodiment the strain is in the form of a bacterial broth.

In another embodiment the strain is in the form of a freeze-dried powder.

The invention provides a formulation which comprises a strain of the invention.

The formulation may further comprise another probiotic material.

The formulation may further comprise a prebiotic material.

The formulation may further comprise an ingestible carrier.

In one case the ingestible carrier is a pharmaceutically acceptable carrier such as a capsule, tablet or powder.

In another case the ingestible carrier is a food product such as acidified milk, yoghurt, frozen yoghurt, milk powder, milk concentrate, ice cream, cheese spreads, dressings or beverages.

In some embodiments the formulation further comprises a protein and/or peptide, in particular proteins and/or peptides that are rich in glutamine/glutamate, a lipid, a carbohydrate, a vitamin, mineral and/or trace element.

In one case the strain is present in an amount of more than $10^6$ cfu per gram of the formulation.

The formulation may further comprise an adjuvant.

The formulation may further comprise a bacterial component.

The formulation may further comprise a drug entity.

The formulation may further comprise a biological compound.

The invention also provides a foodstuff comprising a strain or a formulation of the invention.

Also provided is a medicament comprising a strain or a formulation of the invention.

In one embodiment the formulation further comprises a carbohydrate.

The formulation may comprise an oligosaccharide which may be non-digestible.

In one case the oligosaccharide comprises raffinose.

The invention also provides a method for enhancing the microbiota of an individual who is a member of industrialised human society comprising the step of administering a strain of *Lactobacillus reuteri* which is isolated from an individual who is not a member of industrialised human society.

The microbiota may be the gut microbiota.

The strain may be a strain as defined herein.

The strain may be a component of a formulation as defined herein.

In one embodiment the method comprises administering a carbohydrate substrate for the strain. The substrate may comprise an oligosaccharide which may be non-digestible. In one case the oligosaccharide comprises raffinose.

The substrate may be administered at the same time or separately from the strain.

It will be appreciated that the strains of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

The invention also includes mutants and variants of the deposited strains. Throughout the specification the terms mutant, variant and genetically modified mutant include a strain whose genetic and/or phenotypic properties are altered compared to the parent strain. Naturally occurring variant includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

BRIEF DESCRIPTION OF THE DRAWINGS

The invention will be more clearly understood from the following description thereof given by way of example only with reference to the accompanying drawings in which;—

FIG. 8 is a Principle component analysis (PCA) plot of cytokine response of one dose of *Lactobacillus reuteri* strains in the PBMC assay;

DETAILED DESCRIPTION OF THE INVENTION

A deposit of *Lactobacillus reuteri* strain was made under the terms of the Budapest Treaty at the National Collections of Industrial and Marine Bacteria Limited (NCIMB) Ferguson Building, Craibstone Estate, Bucksbum, Aberdeen, AB21 9YA, Scotland, UK on Sep. 29, 2017 and accorded the accession number NCIMB 42835.

EXAMPLES

The following examples further describe and demonstrate embodiments within the scope of the invention. The examples are given solely for illustration and are not to be construed as limitations of the present invention, as many variations thereof are possible without departing from the spirit and scope of the invention.

A New Phylogenetic Clade

Figure 1:
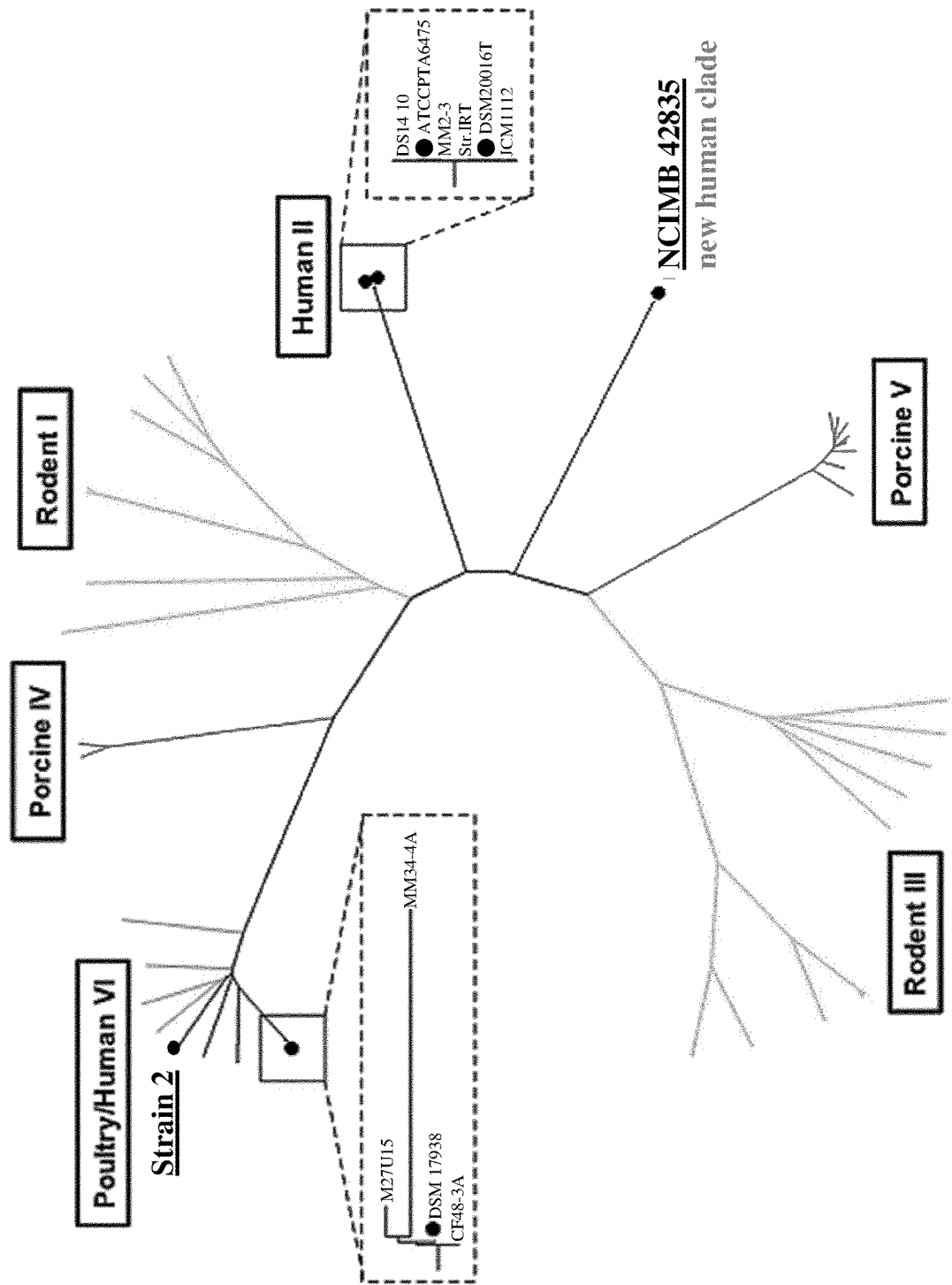
FIG. 1 is an illustration of a phylogenetic tree of new and published *Lactobacillus reuteri* genomes (n=54) derived from multiple hosts. The phylogenetic tree was constructed based on the alignments of all core genes (n=639). Genealogy inferred by ClonalFrame from MLSA data (Bayesian method with exclusion of recombinant regions)

*L. reuteri* was regularly detected in humans in studies conducted around 1960 but is very rarely found in contemporary humans, suggesting a recent decline of the *L. reuteri* population in Westerners (Walter et al., 2011). *L. reuteri* is a real symbiont of vertebrates that has evolved a high level of specificity with its respective host species, pointing to a tight relationship that was maintained over evolutionary times (Oh et. al., 2010; Frese et al., 2011; Duar et al., 2017; Frese et al., 2013). Importantly, *L. reuteri* exerts substantial benefits towards host immune functions and development, as demonstrated in a number of high impact publications (Zelante et al. 2013; Buffington et al. 2016; Lamas et al. 2016; He et al. 2017). However, there are less than 20 genomes of western *L. reuteri* strains available in international databases. Most human isolates cluster in one phylogenetic lineage (linage II) (Oh et. al., 2010). The population structure of this lineage is characterized by a very low level of diversity, showing <50 Single Nucleotide Polymorphisms (SNPs) over the available genomes compared to other species (FIG. 1). Overall, these findings suggest a recent decline of the *L. reuteri* population in Westerners and a genetic or population bottleneck.

Figure 2:
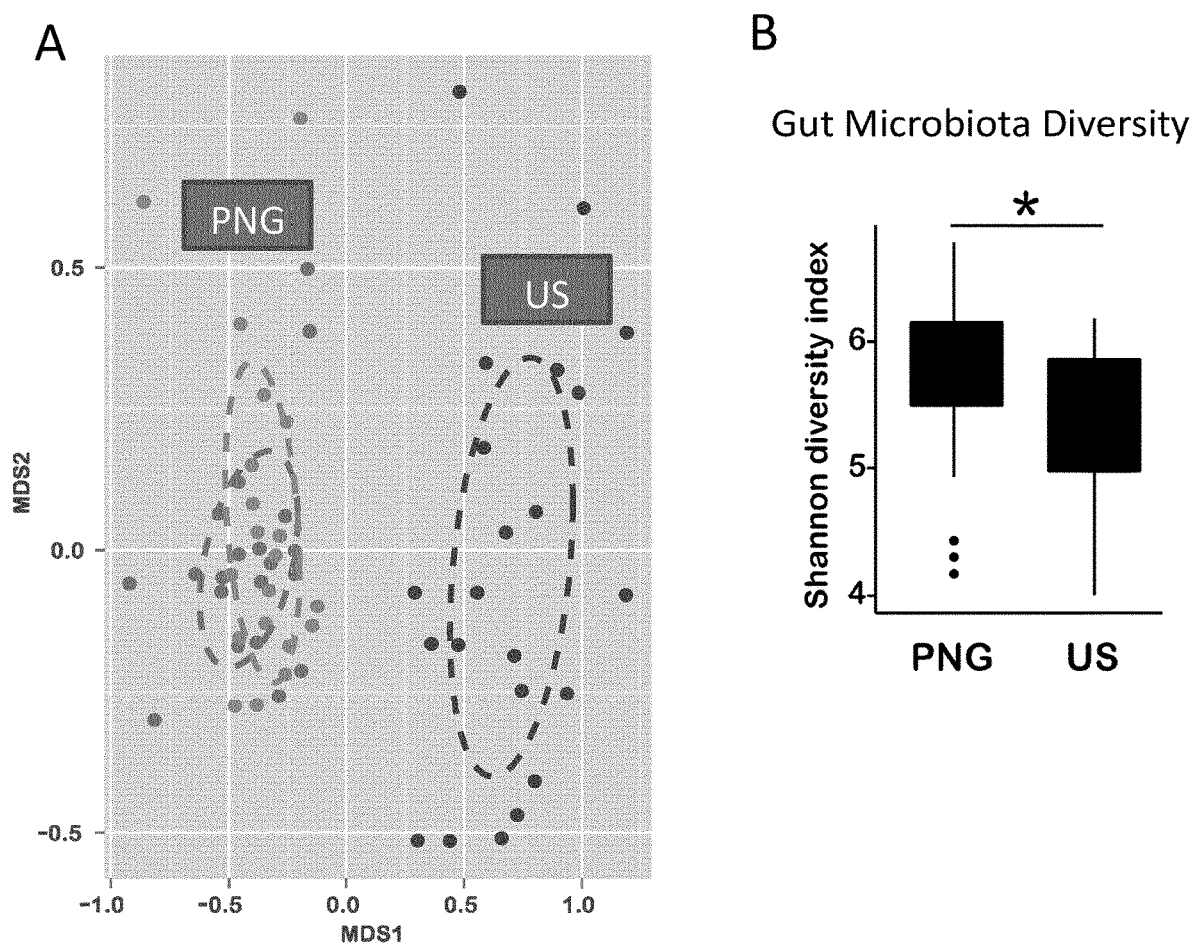
FIG. 2 illustrates the differences in fecal microbiota in rural Papua New Guineans and individuals living in the United States. A) Differences in the overall bacterial population in fecal samples (Bray-Curtis dissimilarity), B) Shannon diversity of bacterial populations (Martinez et al 2015)
Figure 3:
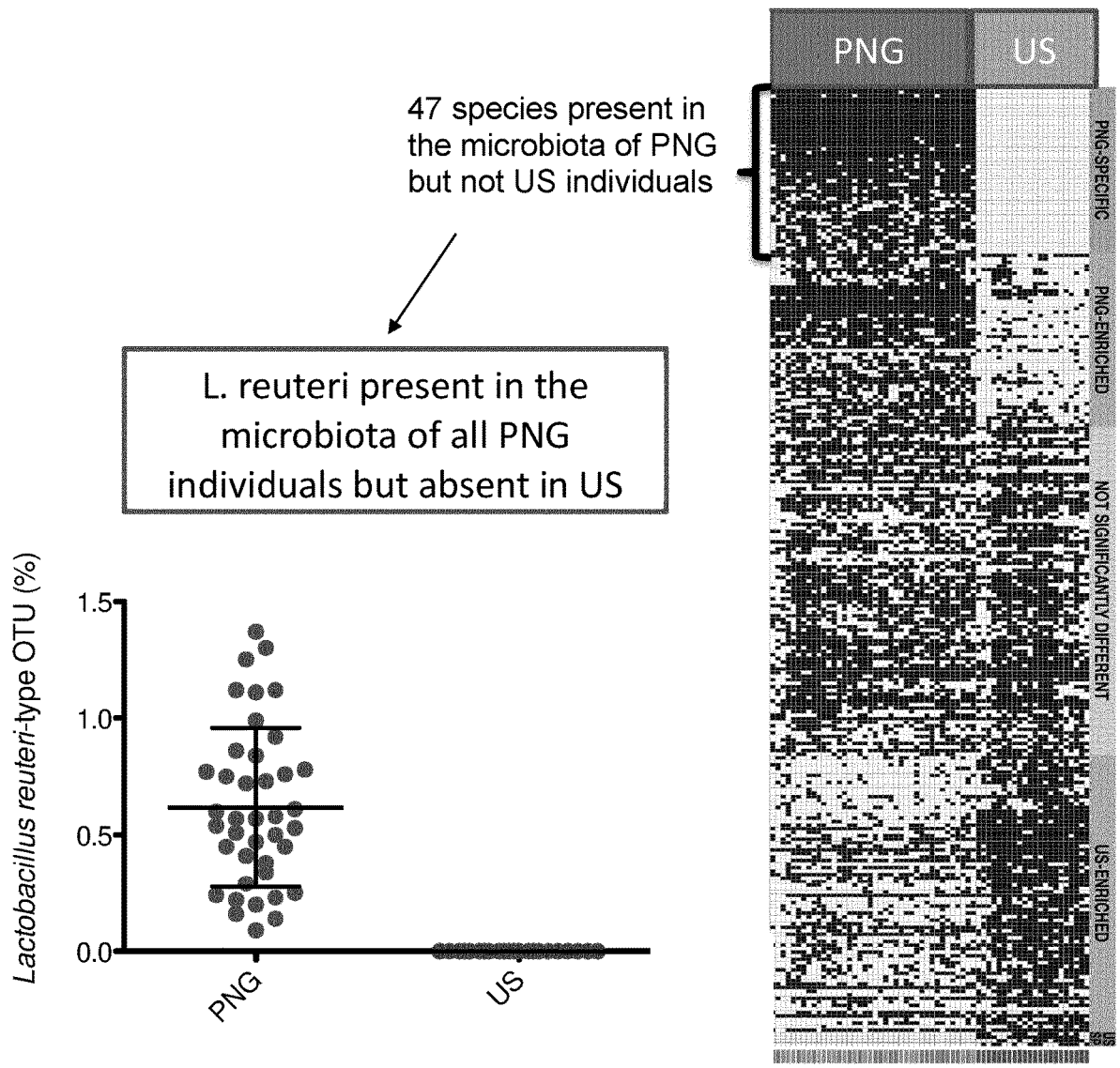
FIG. 3 illustrates the presence of 47 species-level Operational Taxonomic Units (OTUs) in the gut of rural Papua New Guineans that are absent from the gut microbiota on North Americans of which *L. reuteri* is one. The figure highlights the presence of high levels of *L. reuteri* in the gut microbiota of rural Papua New Guineans whereas *L. reuteri* is absence from the gut microbiota of individuals living in the United States.

FIG. 2 illustrates the gut microbiota in rural Papua New Guineans. There is now substantial evidence that modern lifestyle and industrialization has resulted in substantial decrease in the bacterial diversity of the gut microbiota, likely due to a combination of factors such as use of antibiotics, modern clinical practices, sanitation, and change in dietary habits (Blaser & Falkow 2009; Segata, 2015). FIG. 2a shows that the gut microbiota is significantly different between Papua New Guineans and North Americans. FIG. 2b shows the higher diversity in the fecal microbiota of individuals from rural tribes in Papua New Guinea. FIG. 3 illustrates that 47 species-like OTUs are completely undetectable in the gut microbiota of North Americans. This work confirms the overall premise of 'microbiome depletion' in western society. Interestingly, one species detectable in every Papua New Guinean individual by 16S rRNA sequencing but not in a single US control is *Lactobacillus reuteri* (FIG. 3). Western non-communicable diseases, such as Autism and IBD, were virtually absent in Papua New Guinea (although they have been emerging recently due to a transmission to a more urbanized lifestyle). We have investigated isolates of *L. reuteri* that were obtained from fecal samples of rural Papua New Guineans and identified a new *L. reuteri* strain that differs significantly from *L. reuteri* strains isolated from western humans. *L. reuteri* strains from tribespeople in Papua New Guinea have never been isolated or characterized before.

To obtain full-length 16S rRNA gene sequences, the assembly of each strain was aligned to the 16S rRNA gene sequence of DSM 20016T using BLAST, and those aligned sequence fragments were further assembled manually. Similarity values among 16S rRNA genes were calculated using BLAST. The findings of this analysis showed that PB-W1 shared >99.5% sequence identity with the other strains of *L. reuteri*, which included the type strain of the species, demonstrating conclusively that the strain is an *L. reuteri*.

Further genomic analysis and comparison of the *L. reuteri* strain isolated from rural Papua New Guineans to *L. reuteri* strains from western humans indicates that the genome sequence of *L. reuteri* NCIMB 42835 is >2.5% different from any known human *L. reuteri* based on Average Nucleotide Identity (ANI) (Table 1). In particular, *L. reuteri* NCIMB 42835 does not fall within any of the established phylogenic linkages within the *L. reuteri* phylogenic tree (FIG. 1). Thus *L. reuteri* NCIMB 42835 represents a newly identified clade.

In contrast, *L. reuteri* strain 2 which was also isolated from rural Papua New Guineans belongs to clade VI.

TABLE 1

| Western human Strains | Non-western *L. reuteri* NCIMB 42835 Average Nucleotide Identity[1] |
|---|---|
| *L. reuteri* PTA 6475 | 97.42 |
| *L. reuteri* DSM20016[T] | 97.42 |
| *L. reuteri* str_IRT | 96.72 |
| *L. reuteri* DSM 17938[2] | 96.50 |

The Roary pipeline was applied to identify core genes based on annotated assemblies of novel and published *L. reuteri* genomes (n=54). Average nucleotide sequence identity (ANI) values among 5 different strains were calculated based on these concatenated core genes in JSpeciesWS (http://jspecies.ribohost.com/jspeciesws/#analyse/) with BLAST algorithm.

Summary of Findings

The overall 16S 99.5% similarity at species level indicates that PB-W1 can be assigned to the species *L. reuteri*. The ANI result shows substantial strain level variation when NCIMB 42835 is compared to known strains (>2.5% average difference in core genes of the whole genome). This difference confirms that *L. reuteri* NCIMB 42835 does not fall within any of the established phylogenic linkages within the *L. reuteri* phylogenic tree thus *L. reuteri* NCIMB 42835 represents a newly identified clade.

Further Genomic Analysis

The 16s, ITS and IGS regions of NCIMB 42835 were isolated from the whole genome of NCIMB 42835. All regions withdrawn from the whole genome identified the strain as be a member of the *L. reuteri* species.

16s rRNA Identification 16s rRNA identification of NCIMB 42835 was carried out using in silico methods. The genome of NCIMB 42835 was obtained using the Illumina sequencing platform https://www.illumina.com/science/technology/next-generation-sequencing/sequencing-technology.html along with Nanopore technology https://nanoporetech.com/ resulting in 22× coverage of the genome. The NCIMB 42835 strain was mined for the presence of universal 16s rRNA primer set CO1 5' AGTTTGATCCTGGCTCAG 3' (SEQ ID No. 1). and CO2 5' TACCTTGTTACGACT 3'(SEQ ID No. 2). Artemis, a genome visualisation tool was employed as described by Carver et al to facilitate the identification of the 16s rRNA region. Both primers were identified within the genome of NCIMB 42835. The sequence data was then searched against the NCBI nucleotide database to determine the identity of the species of the strain by nucleotide homology. The DNA sequence was subjected to the NCBI standard nucleotide-to-nucleotide homology BLAST search engine https://blast.ncbi.nlm.nih.gov/Blast.cgi. The closet match to the 16s rRNA gene identified the strain to be a member of the *L. reuteri* species.

TABLE 2

16s rRNA sequence of *L. reuteri* NCIMB 42835 (SEQ ID No. 3).

```
TTATATATTTTATATGAGAGTTTGATCCTGGCTCAGGATGAACGCCGGCGGTGTGCCTAATACATGCAAGTCGTAC
GCACTGGCCCAACTGATTGATGGTGCTTGCACCTGATTGACGATGGATCACCAGTGAGTGGCGGACGGGTGAGTA
ACACGTAGGTAACCTGCCCCGGAGCGGGGGATAACATTTGGAAACAGATGCTAATACCGCATAACAACAAAAGCC
ACATGGCTTTTGTTTGAAAGATGGCTTTGGCTATCACTCTGGGATGGACCTGCGGTGCATTAGCTAGTTGGTAAGG
TAACGGCTTACCAAGGCGATGATGCATAGCCGAGTTGAGAGACTGATCGGCCACAATGGAACTGAGACACGGTC
CATACTCCTACGGGAGGCAGCAGTAGGGAATCTTCCACAATGGGCGCAAGCCTGATGGAGCAACACCGCGTGAG
TGAAGAAGGGTTTCGGCTCGTAAAGCTCTGTTGTTGGAGAAGAACGTGCGTGAGAGTAACTGTTCACGCAGTGAC
GGTATCCAACCAGAAAGTCACGGCTAACTACGTGCCAGCAGCCGCGGTAATACGTAGGTGGCAAGCGTTATCCGG
ATTTATTGGGCGTAAAGCGAGCGCAGGCGGTTGCTTAGGTCTGATGTGAAAGCCTTCGGCTTAACCGAAGAAGTG
CATCGGAAACCGGGCGACTTGAGTGCAGAAGAGGACAGTGGAACTCCATGTGTAGCGGTGGAATGCGTAGATAT
ATGGAAGAACACCAGTGGCGAAGGCGGCTGTCTGGTCTGCAACTGACGCTGAGGCTCGAAAGCATGGGTAGCGA
ACAGGATTAGATACCCTGGTAGTCCATGCCGTAAACGATGAGTGCTAGGTGTTGGAGGGTTTCCGCCCTTCAGTG
CCGGAGCTAACGCATTAAGCACTCCGCCTGGGGAGTACGACCGCAAGGTTGAAACTCAAAGGAATTGACGGGGG
CCCGCACAAGCGGTGGAGCATGTGGTTTAATTCGAAGCTACGCGAAGAACCTTACCAGGTCTTGACATCTTGCGCT
AACCTTAGAGATAAGGCGTTCCCTTCGGGGACGCAATGACAGGTGGTGCATGGTCGTCGTCAGCTCGTGTCGTGA
GATGTTGGGTTAAGTCCCGCAACGAGCGCAACCCTTGTTACTAGTTGCCAGCATTAAGTTGGGCACTCTAGTGAGA
CTGCCGGTGACAAACCGGAGGAAGGTGGGGACGACGTCAGATCATCATGCCCCTTATGACCTGGGCTACACACGT
GCTACAATGGACGGTACAACGAGTCGCAAACTCGCGAGAGCAAGCTAATCTCTTAAAGCCGTTCTCAGTTCGGAC
TGTAGGCTGCAACTCGCCTACACGAAGTCGGAATCGCTAGTAATCGCGGATCAGCATGCCGCGGTGAATACGTTC
CCGGGCCTTGTACACACCGCCCGTCACACCATGGGAGTTTGTAACGCCCAAAGTCGGTGGCCTAACCTTTATGGAG
GGAGCCGCCTAAGGCGGGACAGATGACTGGGGTGAAGTCGTAACAAGGTAGCCGTAGGAAACCTGCGGCTGGA
TC
```

Internal Transcribed Spacer (ITS) Profiling:

The NCIMB 42835 strain was mined for the presence of *Lactobacillus* universal ITS primers Probio-lac_Uni 5' CGTAACAAGGTAGCCGTAGG 3' (SEQ ID No. 4). and Probio-lac_Rev 5' GTYVCGTCCTTCWTCGSC 3' (SEQ ID No. 5), obtained from a study carried out by Milani et al., 2018. A genome visualisation tool, Artemis as described by Carver et al, was employed to facilitate the identification of the ITS primer set. Both primers were identified within the genome of NCIMB 42835.

The sequence data was then searched against the NCBI nucleotide database to determine the identity of the species of the strain by nucleotide homology. The DNA sequence was subjected to the NCBI standard nucleotide-to-nucleotide homology BLAST search engine. The closet match to the ITS sequence data obtained identified the strain to be a member of the *L. reuteri* species.

TABLE 3

ITS sequence of *L. reuteri* NCIMB 42835 (SEQ ID No. 6).

```
TAGTACCAAGGCATTCACCATGCGCCCTTCATAACTTAACCTAAACAATCAAAGATTGTC
TGATTAATTGAGTTAGCGATTATAATTCGTTAATTAAAACTCAAATAACGCGGTGTTCTC
GGTTTATTGTTTTGTTAATAAAGAAATTAGATAGTATTTAGTTTTCAAAGTACAAGCTCT
GAGGGTAAACCCCTCAAAACTAAACAAAGTTTCTTTGATGTGTAGGTTCCGTTTTATTCC
TTAGAAAGGAGGTGATCCAGCCGCAGGTTCTCC
```

InterGenic Spacer (IGS)

The NCIMB 42835 strain was mined for the presence of a *Lactobacillus* IGS primer set. The 16S-23S intergenic spacer region isolate was identified using primers that would anneal to conserved regions of the 16S and 23S genes; 16-1A 5'-GAATCGCTAGTAATCG-3' (SEQ ID No. 7) and 23-1B 5'-GGGTTCCCCCATTCGGA-3' (SEQ ID No. 8). The primer set was obtained from a study conducted by Tannock et al., 1999. A genome visualisation tool, Artemis as described by Carver et al, was employed to facilitate the identification of the IGS primer set. Both primers were identified within the genome of NCIMB 42835.

The sequence data obtained was then searched against the NCBI nucleotide database to determine the identity of the species of the strain by nucleotide homology. The DNA sequence was subjected to the NCBI standard nucleotide-to-nucleotide homology BLAST search engine. The closet match to the IGS sequence data obtained identified the strain to be a member of the *L. reuteri* species.

TABLE 4

IGS sequence of *L. reuteri* NCIMB 42835 (SEQ ID No. 9).

```
AATCTCCGGATCAAAGCGTACTTACCGCTCCCCGAAGCATATCGGTGTTAGTCCCGTCC
TTCATCGGCTCCTAGTACCAAGGCATTCACCATGCGCCCTTCATAACTTAACCTAAACAA
TCAAAGATTGTCTGATTAATTGAGTTAGCGATTATAATTCGTTAATTAAAACTCAAATAA
CGCGGTGTTCTCGGTTTATTGTTTTGTTAATAAAGAAATTAGATAGTATTTAGTTTTCAA
AGTACAAGCTCTGAGGGTAAACCCCTCAAAACTAAACAAAGTTTCTTTGATGTGTAGGTT
```

TABLE 4-continued

IGS sequence of L. reuteri NCIMB 42835 (SEQ ID No. 9).

```
CCGTTTTATTCCTTAGAAAGGAGGTGATCCAGCCGCAGGTTCTCCTACGGCTACCTTGTT
ACGACTTCACCCCAGTCATCTGTCCCGCCTTAGGCGGCTCCCTCCATAAAGGTTAGGCCA
CCGACTTTGGGCGTTACAAACTCCCATGGTGTGACGGGCGGTGTGTACAAGGCCCGGGAA
CGTATTCACCGCGGCATGCTGATCCGCG
```

NCIMB 42835 Induces Different Cytokine Responses in Human Immune Cells

We have complemented these genomic comparisons with functional data on the effects of L. reuteri strains on cytokine production by human immune cells (PBMCs). The analysis shows that strains from the same phylogenetic lineage show similar responses, indicating that the evolutionary history of L. reuteri strains influences their interactions with the host in agreement with previous findings (Spinler et al., 2014). The findings further demonstrate clear differences between NCIMB 42835 and strains from the other two sub-populations of human-derived probiotic L. reuteri.

Studies of neonates born in areas of the developing world with very high microbial burden, such as Papua New Guinea (PNG), show extensive differences in neonatal immune function compared with newborns in highly developed regions, such as Australia (Lisciandro et al., 2012a; 2012b). At the end of gestation, antigen-presenting cells (APC's) from PNG neonates already show much higher baseline expression of markers of activation (HLA-DR and CD86) and inhibition (immunoglobulin-like transcripts 3 and 4) compared with Australian newborns. The immunostimulatory nature of the microbial burden in the PNG environment could be one possible reason for this increased baseline level of markers of activation on APC's. However, on activation, APCs' from PNG cord blood are relatively quiescent with reduced activation and antigen processing and evoke an attenuated T-cell response compared with Australian neonates. Although there are many environmental differences between these settings, microbial burden is one of the most striking, and the more tolerogenic responses of PNG newborns might protect against the development of harmful inflammatory responses in early life. In this respect, it is important to emphasize that L. reuteri strains have been shown to be immune-modulatory and induce regulatory T cells in rodent studies (Liu et al., 2013; 2017). By isolating microbes from donors in PNG we are harnessing the immune stimulatory power of these strains which could dampen the further stimulation the baby receives in early life creating an immune tolerogenic state.

These and other experiments of nature all strongly support the role of the prenatal maternal environment in early immune programming and raise the challenging question of how to harness this to improve immune health in the setting of globally increasing propensity for allergy and other chronic inflammatory diseases.

Studies examining different strains have shown that clinical effects are strain-specific (Wickens et al., 2008). This means that interventions such as supplementation with the novel NCIMB 42835 L reuteri from Papua New Guinea natives into a depleted Western Microbiome may have health associated Immune responses (Abrahamson et al., 2012; Van Nimwegen et al 2011; Bisgard et al., 2011).

Lactobacillus reuteri DSM 20016 is the type strain for Lactobacillus reuteri, and Lactobacillus reuteri ATCC PTA 6475 is a commercially available strain and both were isolated from western subjects and are from the Human II clade (FIG. 1). Lactobacillus reuteri DSM 17938 is a commercially available strain which was isolated from the breast milk of a Peruvian Indian and this strain falls into poultry/human clade VI. We isolated a novel strain from native Papua New Guinean subjects, Lactobacillus reuteri NCIMB 42835, who live a non-industrialized lifestyle. The aim of this study was to determine if these strains had a different cytokine profile when incubated with PBMCs from healthy volunteers in vitro.

PBMC Isolation

Peripheral venous whole blood from 3 healthy donors (males between 30 and 45 years old) was collected in sterile EDTA tubes, mixed few times by inversion and diluted 1/1 with sterile PBS. 20 mL of Ficoll into a new sterile 50 mL conical tube was aliquoted for each donor. For each donor, 25 ml of the diluted EDTA-whole blood was layered on top of the Ficoll aliquoted in step 2. Tubes were centrifuged at 800 g for 30 minutes at 4° C. with brake off. The white buffy coat (PBMC layer) below the plasma was collected and cells were washed twice with sterile PBS. The PBMC were resuspended in fresh warm RPMI 10% FBS+1% Penicillin/streptomycin and counted using an automatic cell counter. The number of cells for each donor was adjusted at $1*10^6$ per ml and aliquoted in 24 well-plates.

Strain Preparation

Frozen and lyophilized L. reuteri strains were briefly centrifuged and resuspended with 10 ml of warm RPMI under sterile conditions to make the stock concentration. The top, middle and low concentrations were prepared (100:1) top dose: 1 ml of stock concentration was added to 4.5 ml of complete RPMI. (50:1) medium dose: the top dose was diluted 1:1 with complete RPMI. To make the (10:1) lower dose: Top dose was diluted 1:9.

Incubation and Controls

A PBMC suspension of $5\times10^5$ cells in 500 µl was aliquoted in 24 wells. PBMC's were incubated with 50 µl of strain for 24 hours, in humidified incubator at 5% $CO_2$ (37° C., 95% air, 100% humidity). Supernatants were collected and centrifuged to pellet cells and the clean cell-free conditioned media were moved in a new Eppendorf and stored immediately at −80 C. The controls are represented as: PBMC+Vehicle (strain cryoprotectant).

Luminex Multiplex Immunoassays

Samples were diluted 1/100 in Assay diluent immediately before the assay. For each well, 50 µL of standard or diluted samples were dispensed in the wells+50 µL.

The analytes to be measured were 3 cytokines IL-10, TNF-α, IL-6). The plate was incubated in accordance with the Manufacturer's protocol and read in a Luminex MAGPIX analyser.

Figure 4:
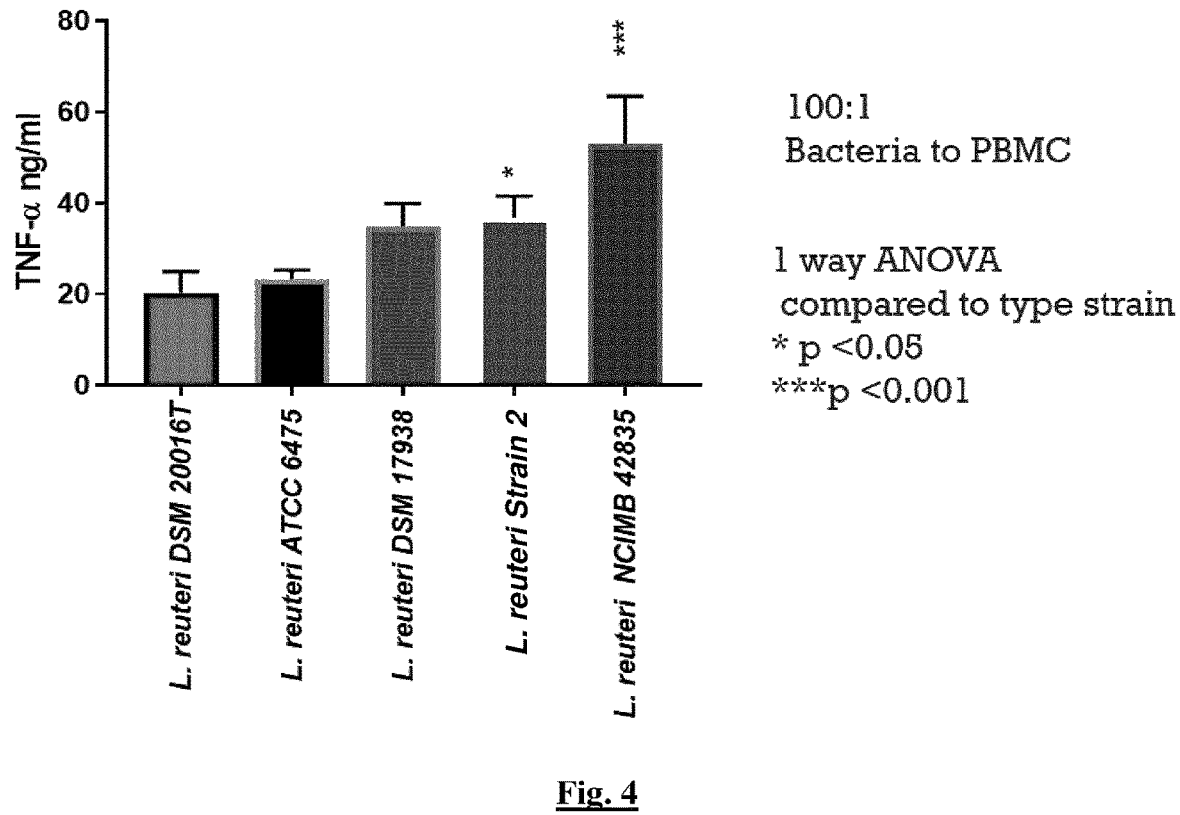
FIG. 4 illustrates the induction profile of TNF-α in PBMC after in vitro stimulation with one concentration of *L. reuteri* DSM 20016, *L. reuteri* ATCC PTA 6475, *L. reuteri* DSM 17938, *L. reuteri* Strain 2 and *L. reuteri* NCIMB 42835.
Figure 5:
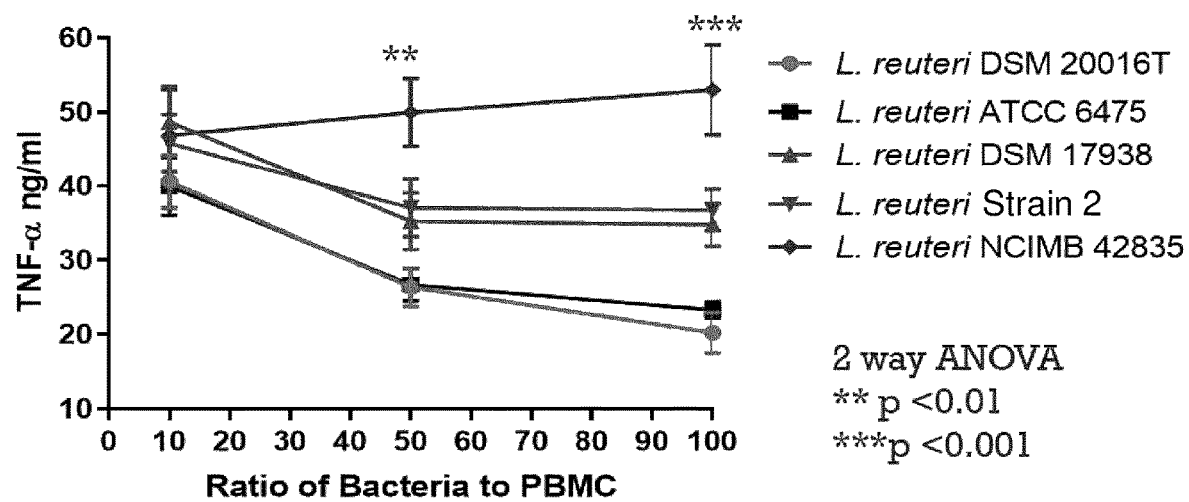
FIG. 5 illustrates the induction profile of TNF-α in PBMC after in vitro stimulation with increasing concentrations of *L. reuteri* DSM 20016, *L. reuteri* ATCC PTA 6475, *L. reuteri* DSM 17938, *L. reuteri* Strain 2 and *L. reuteri* NCIMB 42835.
Figure 6:
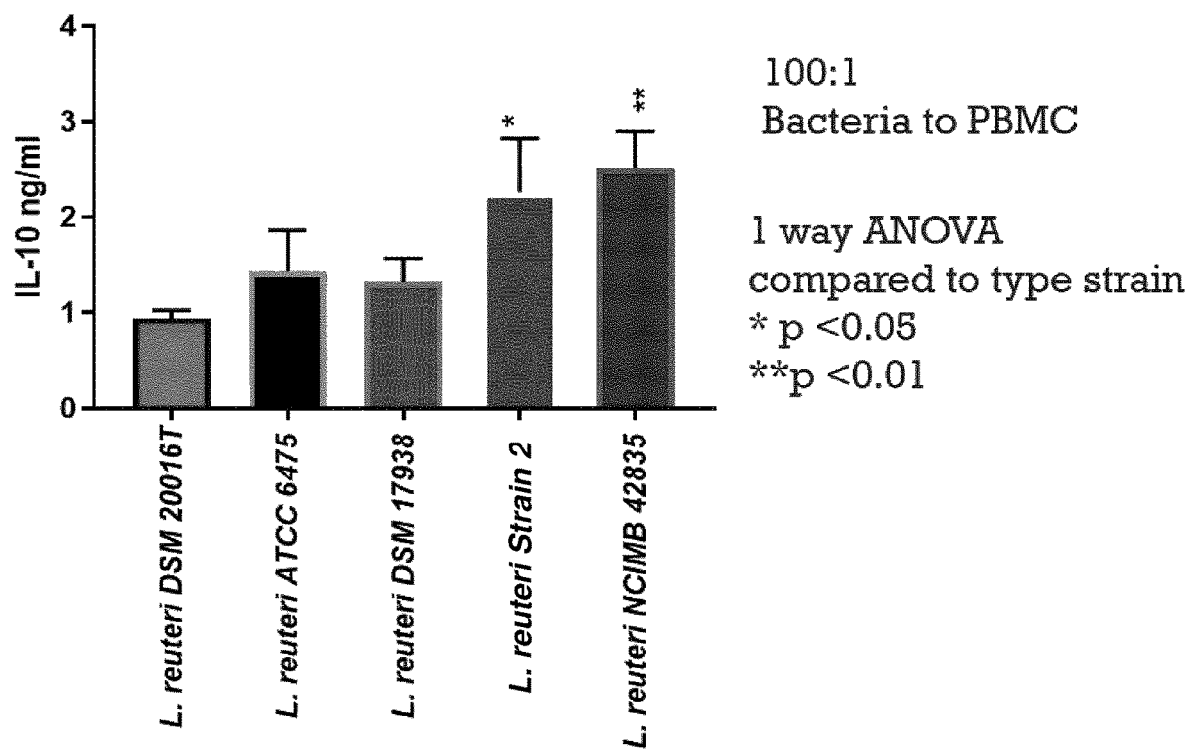
FIG. 6 illustrates the induction profile of IL-10 in PBMC after in vitro stimulation with one concentration of *L. reuteri* DSM 20016, *L. reuteri* ATCC PTA 6475, *L. reuteri* DSM 17938, *L. reuteri* Strain 2 and *L. reuteri* NCIMB 42835.
Figure 7:
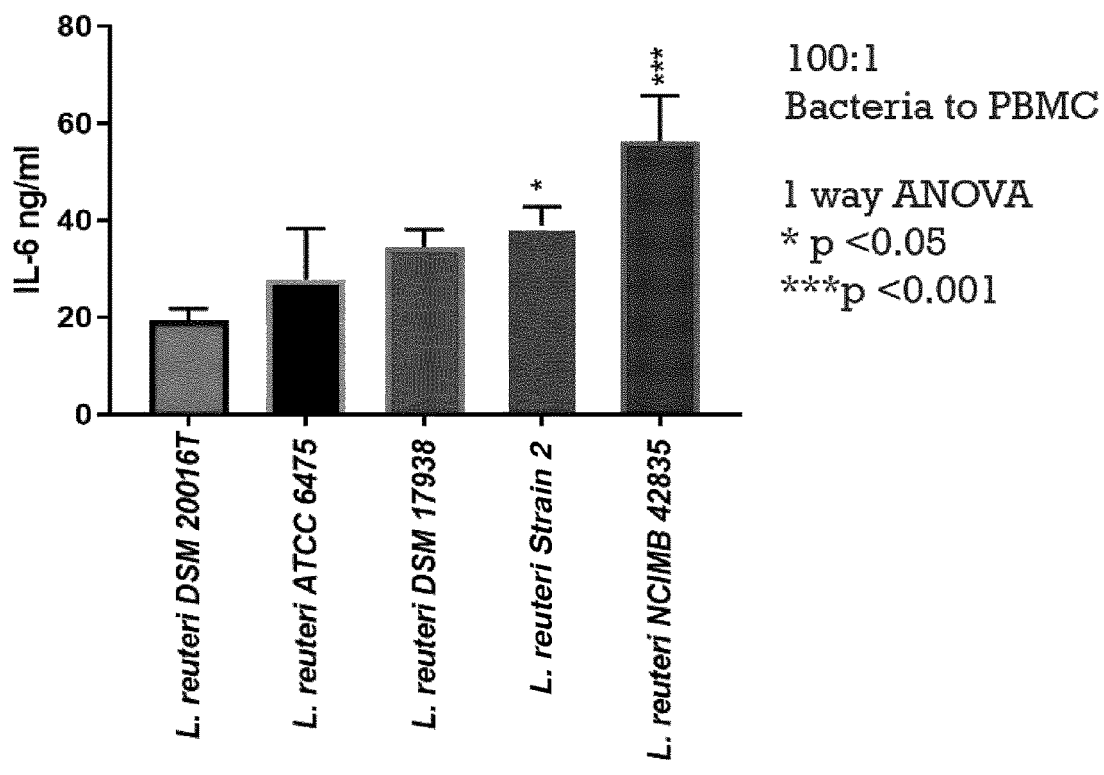
FIG. 7 illustrates the induction profile of IL-6 in PBMC after in vitro stimulation with one concentrations of *L. reuteri* DSM 20016, *L. reuteri* ATCC PTA 6475, *L. reuteri* DSM 17938, *L. reuteri* Strain 2 and *L. reuteri* NCIMB 42835.
Figure 9:
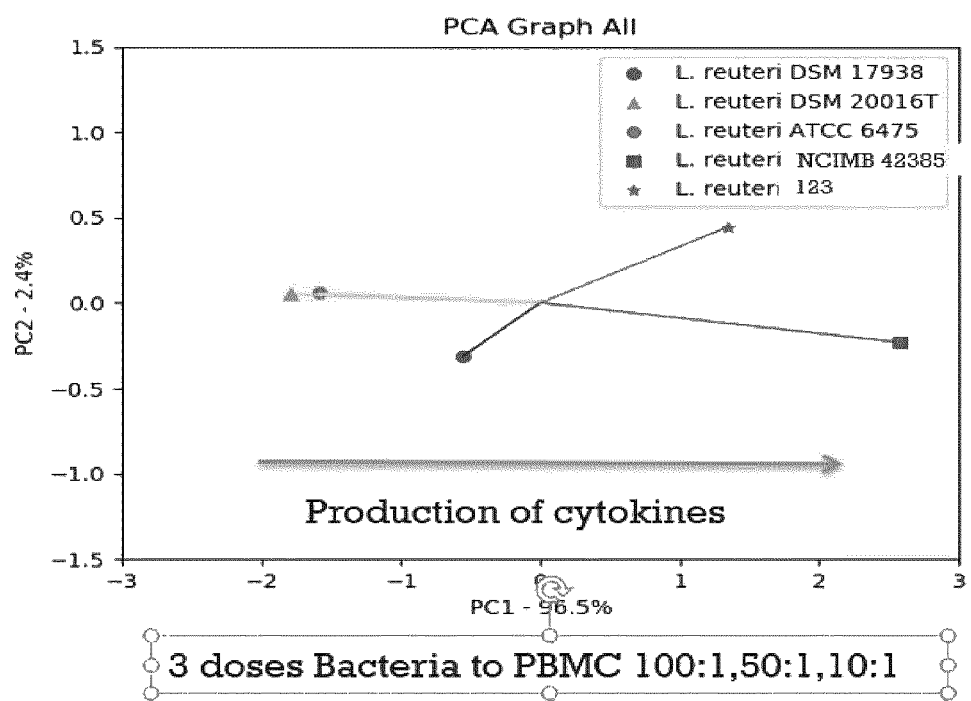
FIG. 9 is a Principle component analysis (PCA) plot of cytokine response of three doses of *Lactobacillus reuteri* strains in the PBMC assay.

Lactobacillus reuteri NCIMB 42835 induced more TNF-α, IL-10, IL-6 from PBMCs than all the other L. reuteri (FIGS. 4,5,6 and 7). When analysing TNF-α induction in PBMCs after all 3 doses of L. reuteri NCIMB 42835 has a unique profile which shows a dose-dependent induction of this cytokine (FIG. 4,5).

Principle component analysis (PCA) is an analysis of principal components of data to visualize the underlying structure of the data where there is the most variance and separation from each other. PCA on the all cytokine data from one dose or from 3 doses of the *L. reuteri* strains found that NCIMB 42835 is the furthest dot to the right of the plot hence showing the highest induction of cytokines. It is the furthest away from the two western strains and it is clearly separated from the other two non-western strains as well which seem half way between the western strains and NCIMB 42835 FIG. 8, 9). The cytokine data agrees with the phylogenetic data showing the NCIMB 42835 is a unique isolate with a strain specific effect on key cytokines in human cells. We have found that NCIMB 42835 which was isolated from a donor in PNG shows immune stimulation as evidenced by increased cytokines levels compared from other *L. reuteri* strains isolated from other regions in the world.

Preferential Use of Certain Carbohydrates by *L. reuteri* NCIMB 42835

Figure 10:
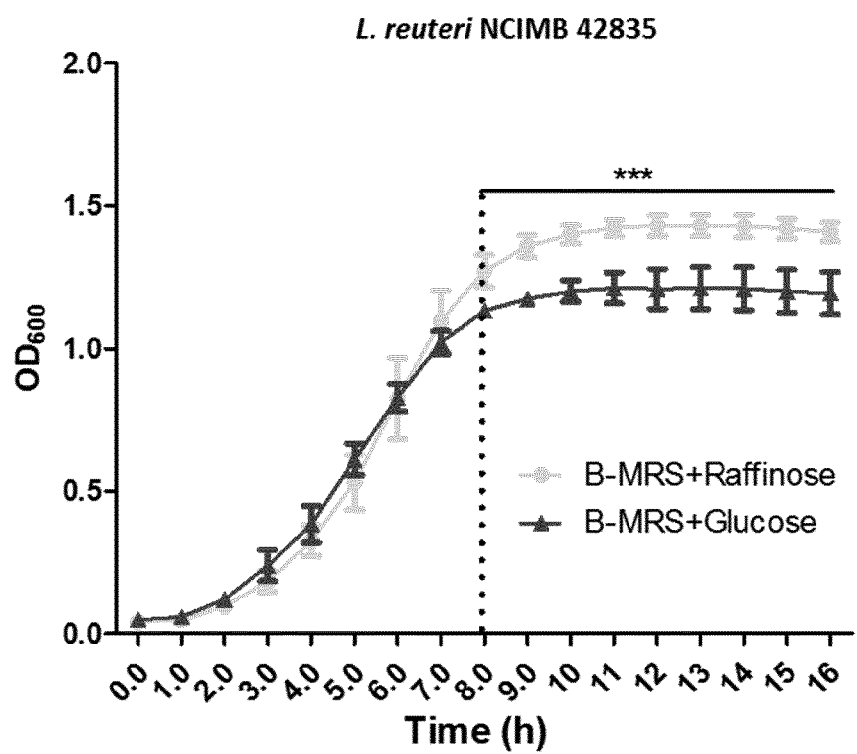
FIG. 10 illustrates growth curves of *L. reuteri* NCIMB 42835 using raffinose or glucose as the sole carbohydrate in basal MRS growth media (3% (m/v)) and demonstrates the preference of *L. reuteri* NCIMB 42835 for raffinose over glucose as a growth substrate in B-MRS. Statistical analysis of OD600 values were performed by GraphPad Prism 5.0 with two-way ANOVA, and P<0.05 was considered as significant. \*\*\*: P<0.001; \*\*: P<0.01; \*: P<0.05.

Carbohydrates such as raffinose are present at very low amounts in western diet, while being abundant in the diet of Papua New Guineans, a population that consumes a predominantly plant-based diet rich in raffinose (a plant based sugar). As mentioned previously, *L. reuteri* are highly adapted and loss of important growth substrates and important traits in western isolates may explain the decline of the *L. reuteri* population in Westerners. The use of raffinose to support the growth *L. reuteri* in the gut has not been previously reported. FIG. 10 shows higher growth for *L. reuteri* NCIMB 42835 on raffinose compared to glucose.

These results demonstrate that raffinose is an excellent growth substrate for the non-western *L. reuteri* strains with superior growth achieved compared to western strain. The use of raffinose in combination with a non-western *L. reuteri* could help to support the re-establishment of this beneficial strain in the gut microbiota of western societies.

*L. reuteri* NCIMB 42835 shows higher persistence than *L. reuteri* DSM20016$^T$ (type strain) in the human gut and benefits from a diet high in raffinose.

To determine if *L. reuteri* NCIMB 42835 shows an adaptation to the human gut and to a plant rich diet, the Walter lab has performed a human study that assesses the performance of the strain in the human gut. The goal of this study is to test the hypothesis that a bacterial species dominant in the non-westernized microbiome can be 'reintroduced' in the gut of Canadians fed a diet designed to promote the growth of the bacteria.

Human trial. Participants were recruited from the University of Alberta Campus and informed consent was obtained. In a three-arm trial design, the effect of two strains of *L. reuteri* (NCIMB 42835 and DSM 20016$^T$) were compared to a placebo group. The impact of a non-western diet is tested as a cross-over design in all study arms. Healthy men and pre-menopausal, non-pregnant and non-lactating women, 18-45 years of age, with a BMI between 20-29.9 kg/m², and no recent history (<3 months) of antibiotic use (N=30). Participants were randomly assigned to 1 of the 3 groups. Groups 1 and 2 will each receive one of the *L. reuteri* strains provided in water for direct consumption, as described by Duar et al. (Duar et al., 2017). Both strains were provided about at a one-time dose of around 10$^{10}$ viable cells, which is a dose by which *L. reuteri* is easily tolerated by humans (Duar et al., 2017). Group three will received a placebo (2 g maltodextrin diluted in water), which is known not to impact microbiome. All groups received a single dose of the probiotic or placebo on day 4 and day 39 of the intervention. Participants will be asked to maintain their usual diet during the one-week screening period. After one week, half of the subjects per arm were assigned to follow the 'non-western diet' (or designed diet), while half continued to consume their usual diet for three weeks (usual diet). After a 2-week washout, participants switched diets, for the second 3-week period of the study. Participants attended a total of 12 clinic visits throughout the course of the study. The baseline visit will occur the day before the commencement of each diet period (days 0 and 35); during these visits, anthropometric, body composition measured by bioelectrical impedance analysis (BIA), blood pressure measurements, blood and stool samples were collected, and participants completed questionnaires on perceived stress and GI tolerance. On study days 4 and 39, participants received the *L. reuteri* strain or placebo according to which group they have been assigned. In addition to the scheduled visits, participants were asked to provide stool samples approximately every two days during each diet period.

Diet. The Walter Lab, in collaboration with other labs at the University of Alberta, designed a dietary intervention that resembles that of individuals following an agrarian lifestyle, while specifically selecting food products that provide indigestible substrates for *L. reuteri*. While a typical western diet is characterized by high intake of red and processed meats, eggs refined grains and sugars, diets of individuals native to Papua New Guinea are comparatively higher in plant based foods, fibre, and carbohydrates, and lower in fat and animal sources of protein (Martinez et al, 2015). Specifically, raffinose is common in the Papua New Guinean diet, but rare in the western diet, and is predicted to support the growth of *L. reuteri* in the human gut (see our preliminary data). While assigned to the non-western (designed) diet period of the study, participants were provided with fully prepared, pre-packaged breakfasts, lunches, dinner and snacks composed of food products that resemble the amounts and type of carbohydrate sources consumed by individuals from an agrarian society (e.g. yam, sweet potato, and cassava), with a total fiber intake of around 42 gram/d per 2000 calories (more than double of the average fiber intake in Canadians). Additionally, the diet was conservative in the amount of animal protein provided (frequency of once daily or less) emphasizing plant sources of protein such as fava beans and split peas.

Production of *L. reuteri* strains for consumption. *L. reuteri* strains were prepared for consumption in Walter lab under food grade conditions, and cell numbers were established prior to the harvest and the dose was standardized as described by Duar et al. (2017) to around 10$^9$ cells per ml and provided to the subjects in spring water.

Determination of *L. reuteri* Cell Numbers in Fecal Samples.

Fecal samples were collected every 2 days (twice before and for two weeks after consumption of the *L. reuteri* or the placebo). Absolute quantification of the *L. reuteri* strains in fecal samples by bacterial culture using LRIM agar. This agar has been shown to be sufficiently selective to quantitatively isolated *L. reuteri* from human fecal samples (Duar et al., 2017).

Figure 11:
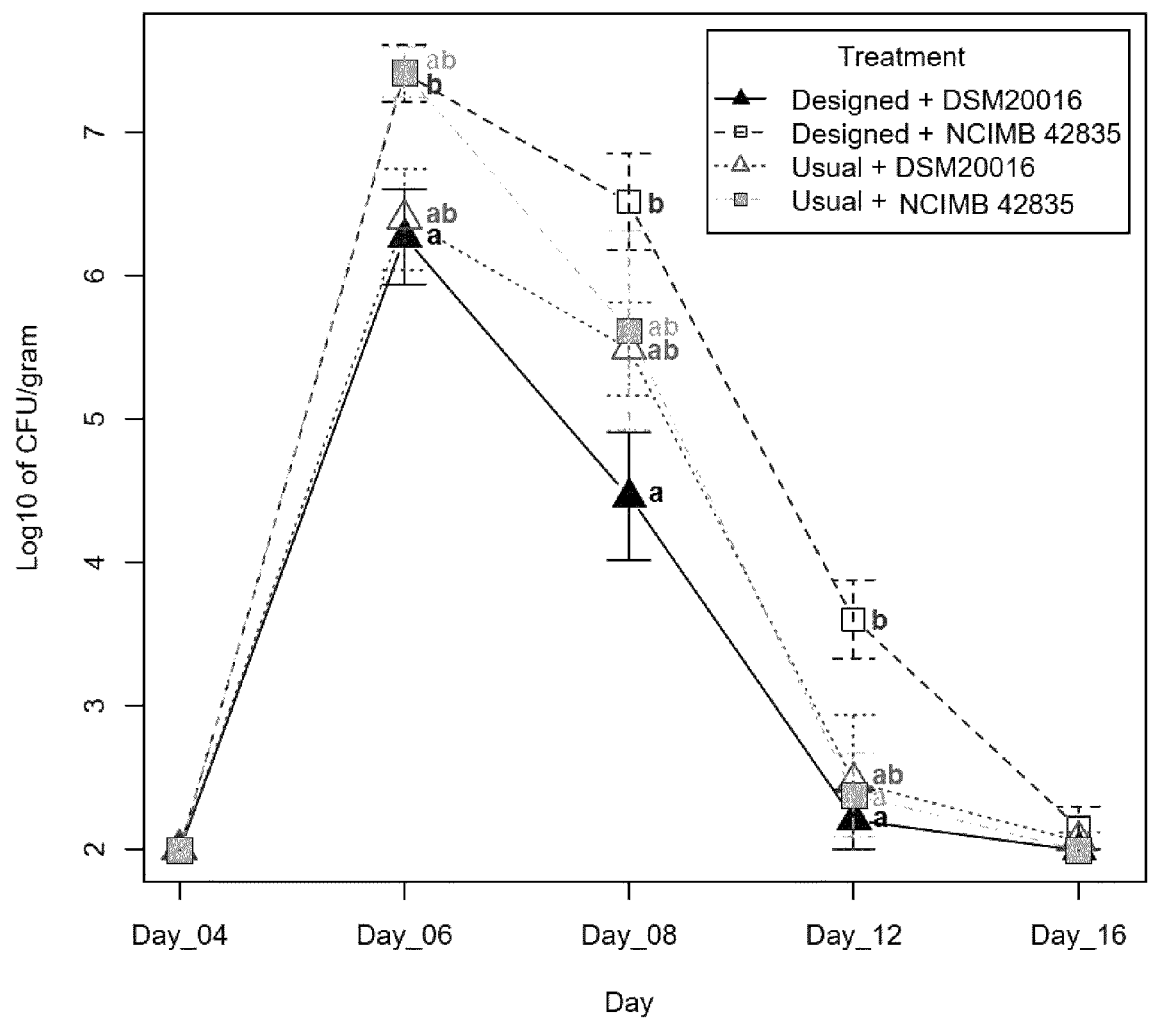
FIG. 11 illustrates the cell numbers of *Lactobacillus reuteri* in fecal samples determined by quantitative plating after a one-time administration of around $10^{10}$ cells of *L. reuteri* at day 4 (n=8 for PB-W1 and n=10 for DSM 20016). Days refer to time after the diet switch to a non-western (designed) during this treatment phase. Data are presented as mean±SE of log 10 of CFU. Within the same day, cell numbers of each treatment labelled with different letters are significantly different based on repeated-measures two-way ANOVA with p<0.05. N.S. not significant.
Figure 12A:
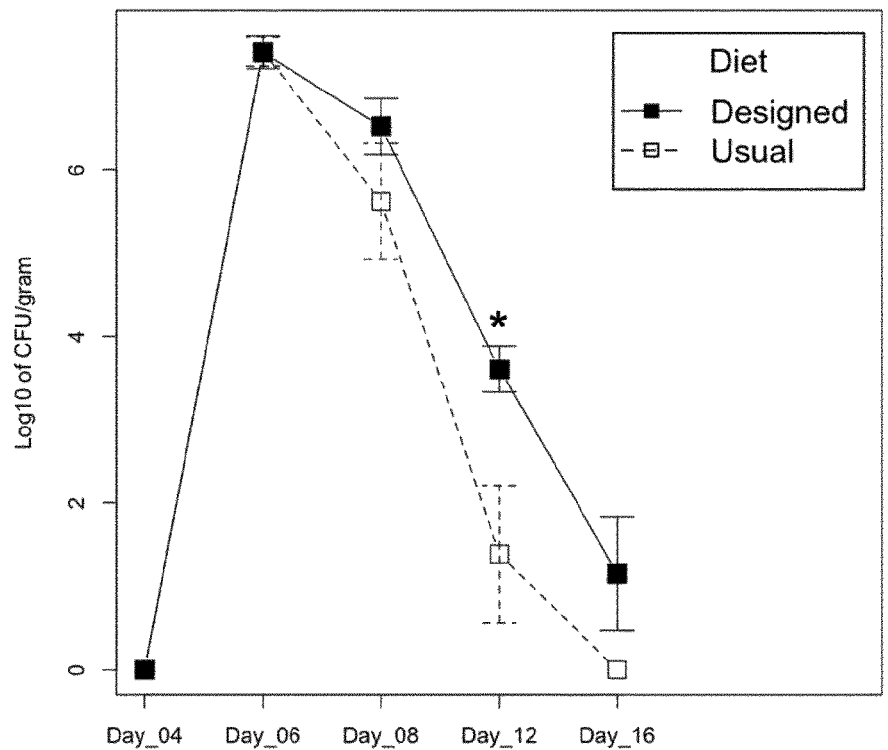
FIG. 12 illustrates the same cell numbers of *Lactobacillus reuteri* in fecal samples determined by quantitative plating separated by strain, comparing cell numbers during the non-western (designed) diet with the usual diet. Cell numbers of *L. reuteri* NCIMB 42835 (n=8) (A) and *L. reuteri* DSM 20016 (n=10) (B) are shown. Data are presented as mean±SE of log 10 of CFU. Within the same day, cell numbers between designed non-western diet and usual diet labelled with \* are significantly different based on paired t-test with p<0.05.
Figure 12B:
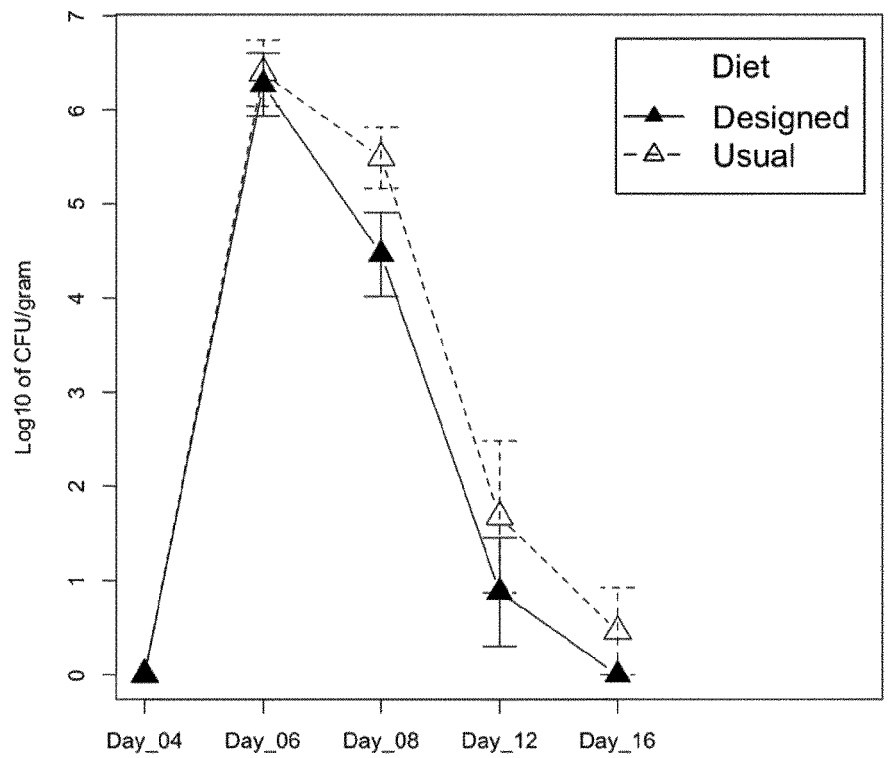

Findings:

As shown in FIG. 11, strain NCIMB 42835 reaches more than 10 fold the cell number when compared with DSM 20016$^T$ two days after administration. Numbers drop afterwards but stay higher for NCIMB 42835 when compared to DSM20016$^T$. In addition, the diet switch to a non-western high plant diet (designed diet) leads to a higher persistence at 8 days after administration (FIGS. 11 and 12A), while DSM2016$^T$ does not gain any benefit from the plant-based diet (FIG. 12B). These findings show that strain NCIMB 42835 has increased fitness in the human gut and benefits from a diet that resamples that of a non-industrialized agrarian human population when compared to the type strain of the species *L. reuteri* (also a human isolate). NCIMB 42835 is established at higher levels, as well as showing an enhanced persistence.

Given that modern lifestyle is associated with substantial increase in chronic disease, redressing lifestyle-induced microbiome depletion has tremendous therapeutic potential. Isolates of *L. reuteri*, originating from rural Papua New Guinea, when put back in the gut of individuals living in industrialized societies, will likely exert health benefits and could help prevent western non-communicable diseases such as autism. In the invention this important symbiont (a species with a long-term evolutionary relationship which results in a mutual benefit) is isolated from non-industrial individuals and demonstrates unique properties. Introduction into the diet of industrialized or westerns humans, which includes its use as a probiotic with and without the parallel administration of substrates such as raffinose has not been proposed before.

It is expected that there will be particular advantages to enhancing the microbiota of infants, young children, a pregnant female or a mother post childbirth.

It will be appreciated that the strains of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

The human immune system plays a significant role in the aetiology and pathology of a vast range of human diseases. Hyper and hypo-immune responsiveness results in, or is a component of, the majority of disease states. One family of biological entities, termed cytokines, are particularly important to the control of immune processes. Perturbances of these delicate cytokine networks are being increasingly associated with many diseases. These diseases include but are not limited to inflammatory disorders, immunodeficiency, inflammatory bowel disease, irritable bowel syndrome, cancer (particularly those of the gastrointestinal and immune systems), diarrhoeal disease, antibiotic associated diarrhoea, paediatric diarrhoea, appendicitis, autoimmune disorders, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and acne vulgaris. The effects on cytokine production are specific for the probiotic strain-examined. Thus specific probiotic strains may be selected for normalising an exclusive cytokine imbalance particular for a specific disease type. Customisation of disease specific therapies can be accomplished using either a single strain or mutants or variants thereof or a selection of these strains.

The enteric microbiota is important to the development and proper function of the intestinal immune system. In the absence of an enteric microbiota, the intestinal immune system is underdeveloped, as demonstrated in germ free animal models, and certain functional parameters are diminished, such as macrophage phagocytic ability and immunoglobulin production. The importance of the gut microbiota in stimulating non-damaging immune responses is becoming more evident. The increase in incidence and severity of allergies in the western world has been linked with an increase in hygiene and sanitation, concomitant with a decrease in the number and range of infectious challenges encountered by the host. This lack of immune stimulation may allow the host to react to non-pathogenic, but antigenic, agents resulting in allergy or autoimmunity. Deliberate consumption of a series of non-pathogenic immunomodulatory bacteria would provide the host with the necessary and appropriate educational stimuli for proper development and control of immune function.

Prebiotics

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. For *L. reuteri*, the most promising prebiotic to be used in combination is raffinose and substrates related to raffinose, such as Alpha-GOS. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), propellants(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in a mixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Intranasal administration can be accomplished using a nasal spray, nasal wash solution or direct application within the nose.

Administration to the lung could be in the form of a dry powder, inhaled using an inhaler device. In some cases the formulation is in the form of an aerosol. The aerosol may be a solution, suspension, spray, mist, vapour, droplets, particles, or a dry powder, for example, using a method dose inhaler including HFA propellant, a metered dose inhaler with non-HFA propellant, a nebulizer, a pressurized can, of a continuous sprayer.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

The invention is not limited to the embodiments hereinbefore described which may be varied in detail.

REFERENCES

Abrahamsson T R, Jakobsson H E, Andersson A F, Björkstén B, Engstrand L, & Jenmalm, M C (2012). Low diversity of the gut microbiota in infants with atopic eczema. *Journal of allergy and clinical immunology*, 129(2), 434-440.

Bisgaard H, Li N, Bonnelykke K, Chawes B L K, Skov T, Paludan-Müller G, . . . & Krogfelt K A (2011). Reduced diversity of the intestinal microbiota during infancy is associated with increased risk of allergic disease at school age. *Journal of Allergy and Clinical Immunology*, 128(3), 646-652.

Blaser M J, Falkow S. (2009). What are the consequences of the disappearing human microbiota? Nat Rev Microbiol. 7(12):887-894. PMID: 19898491.

Buffington S A, Di Prisco G V, Auchtung T A, Ajami N J, Petrosino J F, Costa-Mattioli M. (2016). Microbial reconstitution reverses maternal diet-induced social and synaptic deficits in offspring. Cell 165(7): 1762-1775. PMID: 27315483.

Carver T, Harris S R, Berriman M, Parkhill J, McQuillan J A. Artemis: an integrated platform for visualization and analysis of high-throughput sequence-based experimental data. Bioinformatics. 2012 Feb. 15; 28(4):464-9. doi: 10.1093/bioinformatics/btr703. Epub 2011 Dec. 22. PMID: 22199388; PMCID: PMC3278759.

Duar R M, Frese S A, Lin X B, Fernando S C, Burkey T E, Tasseva G, Peterson D A, Blom J, Wenzel C Q, Szymanski C M, Walter J (2017). Experimental evaluation of host adaptation of *Lactobacillus reuteri* to different vertebrate species. Appl Environ Microbiol. 83(12):e00132-17. PMID: 28389535.

Frese S A, Benson A K, Tannock G W, Loach D M, Kim J, Zhang M, Oh P L, Heng N C, Patil P B, Juge N, MacKenzie D A, Pearson B M, Lapidus A, Dalin E, Tice H, Goltsman E, Land M, Hauser L, Ivanova N, Kyrpides N C, Walter J (2011). The evolution of host specialization in the vertebrate gut symbiont *Lactobacillus reuteri*. PLOS Genetics. 7(2).

Frese S A, MacKenzie D A, Peterson D A, Schmaltz R, Fangman T, Zhou Y, Zhang C, Benson A K, Cody L A, Mulholland F, Juge N, Walter J (2013). Molecular Characterization of Host-Specific Biofilm Formation in a Vertebrate Gut Symbiont. PLOS Genetics.

Hanski I, Von Hertzen L, Fyhrquist N, Koskinen K, Torppa K, Laatikainen T, Karisola P, Auvinen P, Paulin L, Makela M J, Vartiainen E, Kosunin T U, Alenius H, Haahtela T (2012). Environmental biodiversity, human microbiota, and allergy are interrelated. PNAS. 109(21): 8334-8339.

Hatala T, Laatikainen T, Alenius H, Auvinen P, Fyhrquist N, Hanski I, Von Hertzen L, Jousilahti P, Kosunin T U, Markelova O, Makela M J, Pantelejev V, Uhanov M, Zilber E, Vartiainen E (2015). Hunt for the origin of allergy—comparing the Finnish and Russian Karelia. Clinical & amp; Experimental Allergy. 45(5).

He B, Hoang T K, Wang T, Ferris M, Taylor C M, Tian X, Luo M, Tran D Q, Zhou J, Tatevian N, Luo F, Molina J G, Blackburn M R, Gomez T H, Roos S, Rhoads J M, Liu Y. (2017). Resetting microbiota by *Lactobacillus reuteri* inhibits T reg deficiency-induced autoimmunity via adenosine A2A receptors. J Exp Med. 214:107-23. PMID: 27994068.

Jarchum I, Pamer E G. Regulation of innate and adaptive immunity by the commensal microbiota. Curr Opin Immunol 2011; 23:353-60.

Kell, Douglas B., et al. "Viability and activity in readily culturable bacteria: a review and discussion of the practical issues." *Antonie van Leeuwenhoek* 73.2 (1998): 169-187

Lamas B, Richard M L, Leducq V, Pham H P, Michel M L, Da Costa G, Bridonneau C, Jegou S, Hoffmann T W, Natividad J M, Brot L, Taleb S, Couturier-Maillard A, Nion-Larmurier I, Merabtene F, Seksik P, Bourrier A, Cosnes J, Ryffel B, Beaugerie L, Launay J M, Langella P, Xavier R J, Sokol H. (2016). CARD9 impacts colitis by altering gut microbiota metabolism of tryptophan into aryl hydrocarbon receptor ligands. Nat Med. 22(6): 598-605. PMID: 27158904.

Lisciandro J G, Prescott S L, Nadal-Sims M G, Devitt C J, Richmond P C, Pomat W, . . . & van den Biggelaar A H (2012). Neonatal antigen-presenting cells are functionally more quiescent in children born under traditional compared with modern environmental conditions. *Journal of Allergy and Clinical Immunology,* 130(5), 1167-1174.

Lisciandro, J. G., Prescott, S. L., Nadal-Sims, M. G., Devitt, C. J., Pomat, W., Siba, P. M., & van den Biggelaar, A. H. (2012). Comparison of neonatal T regulatory cell function in Papua New Guinean and Australian newborns. *Pediatric Allergy and Immunology,* 23(2), 173-180.

Liu Y, Fatheree N Y, Dingle B M, Tran D Q, Rhoads, J M (2013). *Lactobacillus reuteri* DSM 17938 changes the frequency of Foxp3+ regulatory T cells in the intestine and mesenteric lymph node in experimental necrotizing enterocolitis. *PloS one,* 8(2), e56547.

Liu Y, He B, Hoang T K, Wang T, Taylor C M, Tian X, . . . & Luo F (2017). Therapeutic effect of *Lactobacillus reuteri* DSM 17938 on Treg-deficiency-induced autoimmunity (IPEX syndrome) via the inosine-adenosine 2A receptors.

Marsland J B. (2016). Regulating inflammation with microbial metabolites. Nature Medicine 22:581-583. PMID: 27270775.

Martínez I, Stegen J C, Maldonado-Gomez M X, Eren A M, Siba P M, Greenhill A R, Walter J. (2015). The gut microbiota of rural papua new guineans: composition, diversity patterns, and ecological processes. Cell Rep. 11(4): 527-538. PMID: 25892234.

Milani et al: Christian Milani, Sabrina Duranti, Marta Mangifesta, Gabriele Andrea Lugli, Francesca Turroni, Leonardo Mancabelli, Alice Viappiani, Rosaria Anzalone, Giulia Alessandri, Maria Cristina Ossiprandi, Douwe van Sinderen, Marco Ventura. Phylotype-Level Profiling of Lactobacilli in Highly Complex Environments by Means of an Internal Transcribed Spacer-Based Metagenomic Approach. Applied and Environmental Microbiology July 2018, 84 (14) e00706-18; DOI: 10.1128/AEM.00706-18

Mitsuoka T (1992). Intestinal Flora and Aging. Nutrition Reviews 50(12).

Modern Food Biology 2005 7th edition, James Monroe Jay, Martin J. Loessner, David A. Golden, Springer Science, New York.

Oh P L, Benson A K, Peterson D A, Patil P B, Moriyama E N, Roos S, Walter J (2010). Diversification of the gut symbiont *Lactobacillus reuteri* as a result of host-driven evolution. The ISME Journal. 4: 377-387

Rattanapasert M, Roos S, Hutkins R W, Walter J. Quantitative evaluation of symbiotic strategies to improve persistence and metabolic activity of *Lactobacillus reuteri* DSM17938 in the human gastrointestinal tract. Journal of Functional Foods. 10:85-94 (2014).

Reuter G (2001). The *Lactobacillus* and *Bifidobacterium* microflora of the human intestine: composition and succession. Curr Issues Intest Microbiol. 2(2): 43-53.

Rook G (2013). "The immune system is like an army": An interview with Professor Graham Rook. Gut Microbiota Composition Ruiz-Núñez B, Pruimboom L, Dijck-Brouwer D A, Muskiet F A. (2013). Lifestyle and nutritional imbalances associated with Western diseases: causes and consequences of chronic systemic low-grade inflammation in an evolutionary context. J Nutr Biochem. 24(7): 1183-1201. PMID: 23657158.

Segata N. (2015). Gut microbiome: Westernization and the disappearance of intestinal diversity. Current Biology. 25(14): R611-R613. PMID: 26196489.

Sinkiewicz G, Cronholm S, Ljunggren L, Dahlén G, Bratthall G (2010). Influence of dietary supplementation with *Lactobacillus reuteri* on the oral flora of healthy subjects. Swed Dent J. 34(4): 197-206.

Sonnenburg E D, Sonnenburg J L. (2014). Starving our microbial self: the deleterious consequences of a diet deficient in microbiota-accessible carbohydrates. Cell Metab. 2014, 20(5): 779-786. PMID: 25156449.

Spinler J K., Sontakke A, Hollister E B, Venable S F, Oh P L, Balderas M A, . . . & Versalovic J (2014). From prediction to function using evolutionary genomics: human-specific ecotypes of *Lactobacillus reuteri* have diverse probiotic functions. Genome biology and evolution, 6(7), 1772-1789.

Tannock G W, Tilsala-Timisjarvi A, Rodtong S, Ng J, Munro K, Alatossava T. Identification of *Lactobacillus* isolates from the gastrointestinal tract, silage, and yoghurt by 16S-23S rRNA gene intergenic spacer region sequence comparisons. Appl Environ Microbiol. 1999; 65(9):4264-4267. doi:10.1128/AEM.65.9.4264-4267.1999 van Nimwegen F A, Penders J, Stobberingh E E, Postma D S, Koppelman G H, Kerkhof M, . . . & Mommers M (2011). Mode and place of delivery, gastrointestinal microbiota, and their influence on asthma and atopy. *Journal of Allergy and Clinical Immunology,* 128(5), 948-955.

Walter J, Britton R A, Roos S. (2011). Host-microbial symbiosis in the vertebrate gastrointestinal tract and the *Lactobacillus reuteri* paradigm. Proc Natl Acad Sci USA 108(1): 4645-4652. PMID: 20615995.

Walter J. Ecological Role of Lactobacilli in the Gastrointestinal Tract: Implications for Fundamental and Biomedical Research. American Society for Microbiology.

Wickens K, Black P N, Stanley T V, Mitchell E, Fitzharris P, Tannock G W, . . . & Probiotic Study Group (2008). A differential effect of 2 probiotics in the prevention of eczema and atopy: a double-blind, randomized, placebo-controlled trial. Journal of Allergy and Clinical Immunology, 122(4), 788-794.

Zelante T, Iannitti R G, Cunha C, De Luca A, Giovannini G, Pieraccini G, Zecchi R, D'Angelo C, Massi-Benedetti C, Fallarino A, Puccetti P, Romani L. (2013). Tryptophan catabolites from microbiota engage aryl hydrocarbon receptor and balance mucosal reactivity via interleukin-22. Immunity. 39:372-85. PMID: 23973224.

Zhao X, Gänzle MG (2018). Genetic and phenotypic analysis of carbohydrate metabolism and transport in *Lactobacillus reuteri*. Int J Food Microbiol. 2; 272: 12-21.

The invention claimed is:

1. A formulation comprising a strain of *Lactobacillus reuteri* deposited under NCIMB accession number 42835 mixed with an ingestible carrier, wherein the strain is in the form of a freeze-dried powder, and wherein the formulation is in the form of a capsule, a powder, a food product, or a beverage, the formulation being formulated for oral administration to a subject.

2. The formulation as claimed in claim 1, wherein the formulation further comprises a substrate, and the substrate is a carbohydrate.

3. The formulation as claimed in claim 1, wherein the formulation further comprises a substrate, and the substrate is an oligosaccharide.

4. The formulation as claimed in claim 1, wherein the formulation further comprises a substrate, and the substrate is derived from a plant source.

5. The formulation as claimed in claim 1, wherein the formulation further comprises a substrate, and the substrate comprises raffinose.

6. The formulation as claimed in claim 1, further comprising a prebiotic material.

7. The formulation as claimed in claim 1, wherein the formulation is in the form of a food product chosen from acidified milk, yoghurt, frozen yoghurt, milk powder, milk concentrate, ice cream, a cheese spread, a dressing; or wherein the formulation is in the form of a beverage.

8. A method of treating a subject to increase gut microbiota diversity, the method comprising administering to the subject a formulation comprising *Lactobacillus reuteri* strain having NCIMB accession number 42835, wherein the strain is in the form of a freeze-dried powder, and wherein the formulation increases the gut microbiota diversity in the subject.

9. The method according to claim 8, wherein the subject is an infant, a young child, a pregnant female, or a mother post childbirth.

10. The method according to claim 8, wherein the formulation increases the growth of microbiota in the subject.

11. The method according to claim 8, wherein the formulation is in the form of a capsule, tablet, powder, food product, or beverage.

12. The method according to claim 8, further comprising administering a carbohydrate substrate to the subject.

13. The method according to claim 12, wherein the substrate comprises raffinose.

14. The method according to claim 12, wherein the substrate is administered at the same time as the formulation.

15. The method according to claim 8, wherein the subject has an inflammatory disorder.

16. The formulation according to claim 1, wherein the *Lactobacillus reuteri* strain is in the form of viable cells or non-viable cells.

17. The formulation according to claim 3, wherein the oligosaccharide is non-digestible.

18. The formulation as claimed in claim 1, wherein the strain is a probiotic material and the formulation further comprises a different probiotic material.

19. The formulation as claimed in claim 1, wherein the ingestible carrier comprises alcohol, silicone, a wax, petroleum jelly, a vegetable oil, polyethylene glycol, propylene glycol, a liposome, a sugar, gelatin, lactose, amylase, magnesium stearate, talc, a surfactant, silicic acid, viscous paraffin, perfume oil, a fatty acid monoglyceride, a fatty acid diglyceride, a petroethral fatty acid ester, hydroxymethylcellulose, or polyvinylpyrrolidone.

* * * * *